US 6,564,806 B1

(12) United States Patent
Fogarty et al.

(10) Patent No.: US 6,564,806 B1
(45) Date of Patent: May 20, 2003

(54) DEVICE FOR ACCURATELY MARKING TISSUE

(75) Inventors: Thomas J. Fogarty, 3270 Alpine Rd., Portola Valley, CA (US) 94028; David B. Willis, Palo Alto, CA (US); Thomas A. Howell, Palo Alto, CA (US); George D. Hermann, Portola Valley, CA (US)

(73) Assignee: Thomas J. Fogarty, Portola Valley, CA (US)

( * ) Notice: Subject to any disclaimer, the term of this patent is extended or adjusted under 35 U.S.C. 154(b) by 0 days.

(21) Appl. No.: 09/507,361

(22) Filed: Feb. 18, 2000

(51) Int. Cl.[7] .............................................. A61B 19/00
(52) U.S. Cl. ...................... 128/899; 606/116; 600/434
(58) Field of Search ................. 128/897–899; 600/424, 434; 606/116, 151, 159, 170

(56) References Cited

U.S. PATENT DOCUMENTS

| | | | |
|---|---|---|---|
| 2,022,065 A | 11/1935 | Wapper |
| 2,047,535 A | 7/1936 | Wappler |
| 3,330,278 A | 7/1967 | Santomieri |
| 3,351,463 A | 11/1967 | Rozner et al. |
| 3,516,412 A | 6/1970 | Ackerman |
| 3,714,851 A | 2/1973 | Orser |
| 3,753,700 A | 8/1973 | Harrison et al. |
| 3,890,977 A | 6/1975 | Wilson |
| 4,103,690 A | 8/1978 | Harris |
| 4,274,408 A | 6/1981 | Nimrod |

(List continued on next page.)

FOREIGN PATENT DOCUMENTS

| | | |
|---|---|---|
| EP | 0 385 604 | 5/1990 |
| EP | 0 395 997 | 7/1990 |
| EP | 0 829 232 A2 | 3/1998 |
| EP | 0 829 232 A3 | 3/1998 |
| WO | WO 88/06864 | 9/1988 |

(List continued on next page.)

OTHER PUBLICATIONS

MDTECH product literature, "FlexStrand", product description, Dec. 1999, 1 pg.
MDTECH product literature, "D Wire", product description, Mar. 2000, 2 pgs.
*Auto Suture MIBB\* Site marker: Single use clip applier* (1999). *United States Surgical* © Product instructions).
*Biopsy needles and trays* (1988). *Cook® Diagnostic and Interventional Products* p. 3 (Products price list).
*MIBB\* Site marker* (1999). *United States Surgical* © (Sales brochure).

(List continued on next page.)

*Primary Examiner*—John P. Lacyk
(74) *Attorney, Agent, or Firm*—Morrison & Foerster LLP

(57) ABSTRACT

This invention is an improved tissue localizing device for fixedly yet removably marking a volume of tissue containing a suspect region for excision without penetrating that volume. This invention also encompasses methods for deployment of the localizing device and its excision along with the marked tissue volume. At least one locator element is deployed into tissue and assumes a predetermined curvilinear shape to define a tissue border containing a suspect tissue region along a path. The locator element path preferably encompasses the distalmost portion of the tissue volume without penetrating that volume. Multiple locator elements may be deployed to further define the tissue volume along additional paths defining the tissue volume border that do not penetrate the volume. Polar and tangential deployment configurations as well as a locator element that may be cold-formed by a die in the distal portion of the deployment tube into a permanent arcuate shape is also disclosed.

134 Claims, 21 Drawing Sheets

U.S. PATENT DOCUMENTS

| | | |
|---|---|---|
| 4,341,226 A | 7/1982 | Peters |
| 4,402,328 A | 9/1983 | Doring |
| 4,592,356 A | 6/1986 | Gutierrez |
| 4,595,007 A | 6/1986 | Mericle |
| 4,616,656 A | 10/1986 | Nicholson et al. |
| 4,665,906 A | 5/1987 | Jervis |
| 4,682,606 A | 7/1987 | DeCaprio |
| 4,799,495 A | 1/1989 | Hawkins et al. |
| 4,869,259 A | 9/1989 | Elkins |
| 4,925,445 A | 5/1990 | Sakamoto et al. |
| 4,966,583 A | 10/1990 | Debbas |
| 5,011,473 A | 4/1991 | Gatturna |
| 5,018,530 A | 5/1991 | Rank et al. |
| 5,059,197 A | 10/1991 | Urie et al. |
| 5,067,957 A | 11/1991 | Jervis |
| 5,122,136 A | 6/1992 | Guglielmi et al. |
| 5,158,084 A | 10/1992 | Ghiatas |
| 5,183,463 A | 2/1993 | Debbas |
| 5,190,546 A | 3/1993 | Jervis |
| 5,197,482 A | 3/1993 | Rank et al. |
| 5,205,829 A | 4/1993 | Lituchy |
| 5,221,269 A | 6/1993 | Miller et al. |
| 5,282,845 A | 2/1994 | Bush et al. |
| 5,300,068 A | 4/1994 | Rosar et al. |
| 5,301,682 A | 4/1994 | Debbas |
| 5,353,804 A | 10/1994 | Kornberg et al. |
| 5,409,004 A | 4/1995 | Sloan |
| 5,462,062 A | 10/1995 | Rubinstein et al. |
| 5,472,441 A | 12/1995 | Edwards et al. |
| 5,486,183 A | 1/1996 | Middleman et al. |
| 5,488,958 A | 2/1996 | Topel et al. |
| 5,507,743 A | 4/1996 | Edwards et al. |
| 5,536,267 A | 7/1996 | Edwards et al. |
| 5,540,683 A | 7/1996 | Ichikawa et al. |
| 5,556,410 A | 9/1996 | Mittermeir et al. |
| 5,558,673 A | 9/1996 | Edwards et al. |
| 5,672,173 A | 9/1997 | Gough et al. |
| 5,672,174 A | 9/1997 | Gough et al. |
| 5,683,384 A | 11/1997 | Gough et al. |
| 5,685,853 A | 11/1997 | Bonnet |
| 5,709,697 A | 1/1998 | Ratcliff et al. |
| 5,735,847 A | 4/1998 | Gough et al. |
| 5,741,225 A | 4/1998 | Lax et al. |
| 5,749,887 A | 5/1998 | Heske et al. |
| 5,794,626 A | 8/1998 | Kieturakis |
| 5,795,308 A | 8/1998 | Russin |
| 5,800,484 A | 9/1998 | Gough et al. |
| 5,810,804 A | 9/1998 | Gough et al. |
| 5,853,366 A | 12/1998 | Dowlatshahi |
| 5,855,576 A | 1/1999 | LeVeen et al. |
| 5,863,290 A | 1/1999 | Gough et al. |
| 5,879,357 A | 3/1999 | Heaton et al. |
| 5,882,316 A | 3/1999 | Chu et al. |
| 5,902,310 A | 5/1999 | Foerster et al. |
| 5,904,690 A | 5/1999 | Middleman et al. |
| 5,941,890 A | 8/1999 | Voegele et al. |
| 5,954,655 A | 9/1999 | Hussman |
| 5,989,265 A | 11/1999 | Bouquet De La Joliniere et al. |
| 6,007,495 A | 12/1999 | Matula |
| 6,019,757 A | 2/2000 | Scheldrup |
| 6,022,362 A | 2/2000 | Lee et al. |
| 6,039,735 A | 3/2000 | Greep |
| 6,050,954 A | 4/2000 | Mittermeier |
| 6,051,008 A | 4/2000 | Saadat et al. |
| 6,053,876 A | 4/2000 | Fisher |
| 6,053,925 A | 4/2000 | Barnhart |
| 6,080,113 A | 6/2000 | Heneveld et al. |
| 6,080,114 A | 6/2000 | Russin |

FOREIGN PATENT DOCUMENTS

| | | |
|---|---|---|
| WO | WO 92/12678 | 8/1992 |
| WO | WO 96/27328 | 9/1996 |
| WO | WO 99/04704 | 2/1999 |
| WO | WO 99/25248 A1 | 5/1999 |
| WO | WO 99/43268 | 9/1999 |
| WO | WO 99/44506 A1 | 9/1999 |
| WO | WO 99/58065 A1 | 11/1999 |
| WO | WO 99/66834 A1 | 12/1999 |
| WO | WO 00/10471 A1 | 3/2000 |
| WO | WO 00/12009 A2 | 3/2000 |
| WO | WO 00/12010 | 3/2000 |
| WO | WO 00/13602 | 3/2000 |
| WO | WO 00/16697 | 3/2000 |
| WO | WO 00/24320 A1 | 5/2000 |
| WO | WO 00/28913 | 5/2000 |
| WO | WO 00/30531 | 6/2000 |
| WO | WO 00/33743 | 6/2000 |
| WO | WO 01/05317 | 1/2001 |
| WO | WO 01/05320 | 1/2001 |

OTHER PUBLICATIONS

Homer Mammalok ® Breast Lesion Needle/Wire Localizer (1987). *Namic ® Angiographic Systems Division.* Glens Falls, New York. p. 10. (Hospital products price list).

Urrutia et al. (1988). "Retractable–barb needle for breast lesion localization: use in 60 cases," *Radiology* 169(3):845–847.

Anonymous. *Ariadne's Thread ™ Repositionable Breast Localisation Needle*, (Product Information), one page (date not known).

Anonymous. *Blunt Tubes with Finished Ends. Pointed Cannula, Popper & Sons Biomedical Instrument Division*, (Products Price List), one page (date not known).

Anonymous. *Ground Cannulae, ISPG*, New Milford, CT, (Advertisement), one page (date not known).

Gennari, R. et al. (Jun. 2000). "Use of Technetium–99m–Labeled Colloid Albumin for Preoperative and Intraoperative Localization of Nonpalpable Breast Lesions," *J. Am. Coll. Surg.* 190(6):692–699.

Kopans, D.B. et al. (Nov. ). "Spring Hookwire Breast Lesion Localizer: Use with Rigid–Compression. Mammographic Systems," *Radiology* 157(2):537–538.

Mullan, B.F. et al. (May 1999). "Lung Nodules: Improved Wire for CT–Guided Localization," *Radiology* 211(2):561–565.

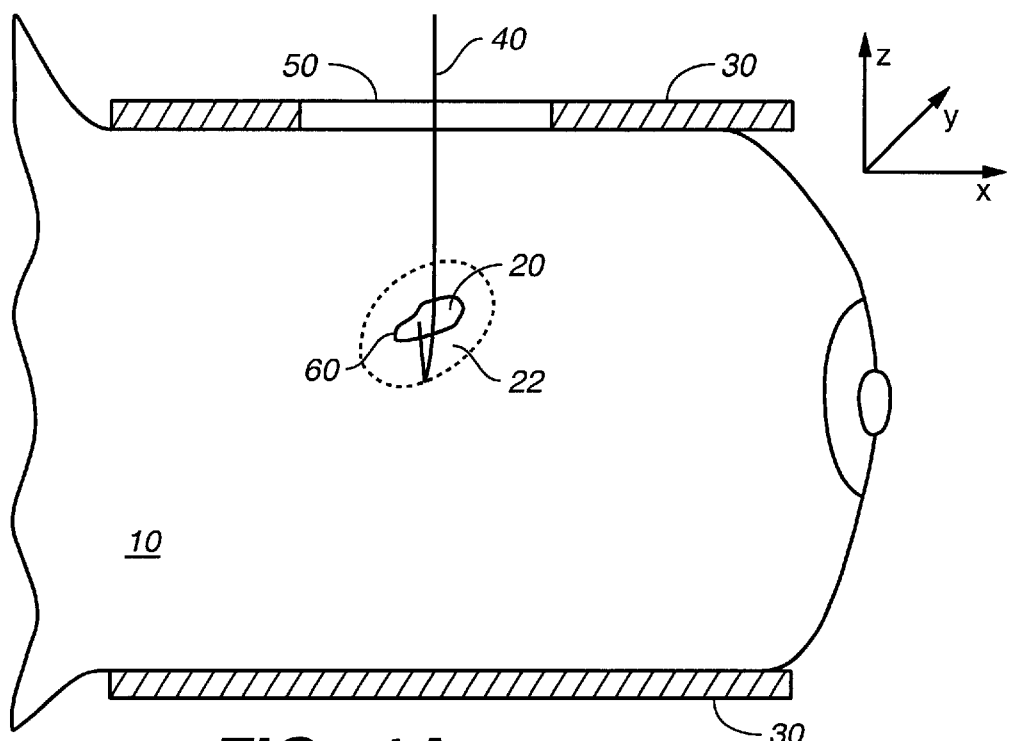
FIG._1A (PRIOR ART)
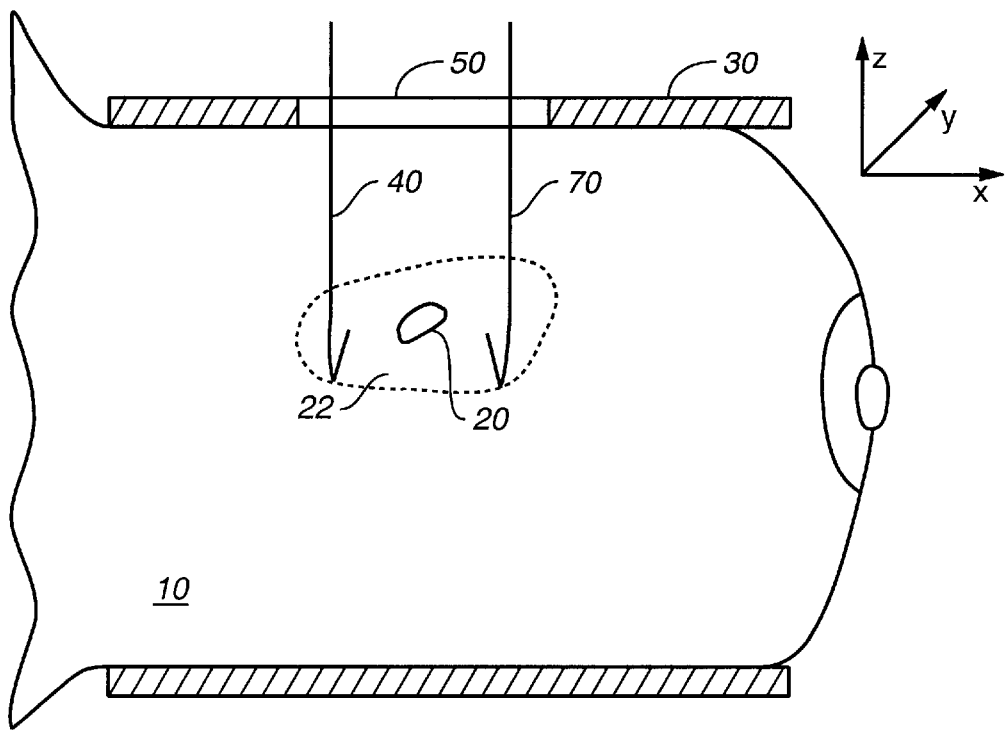
FIG._1B (PRIOR ART)

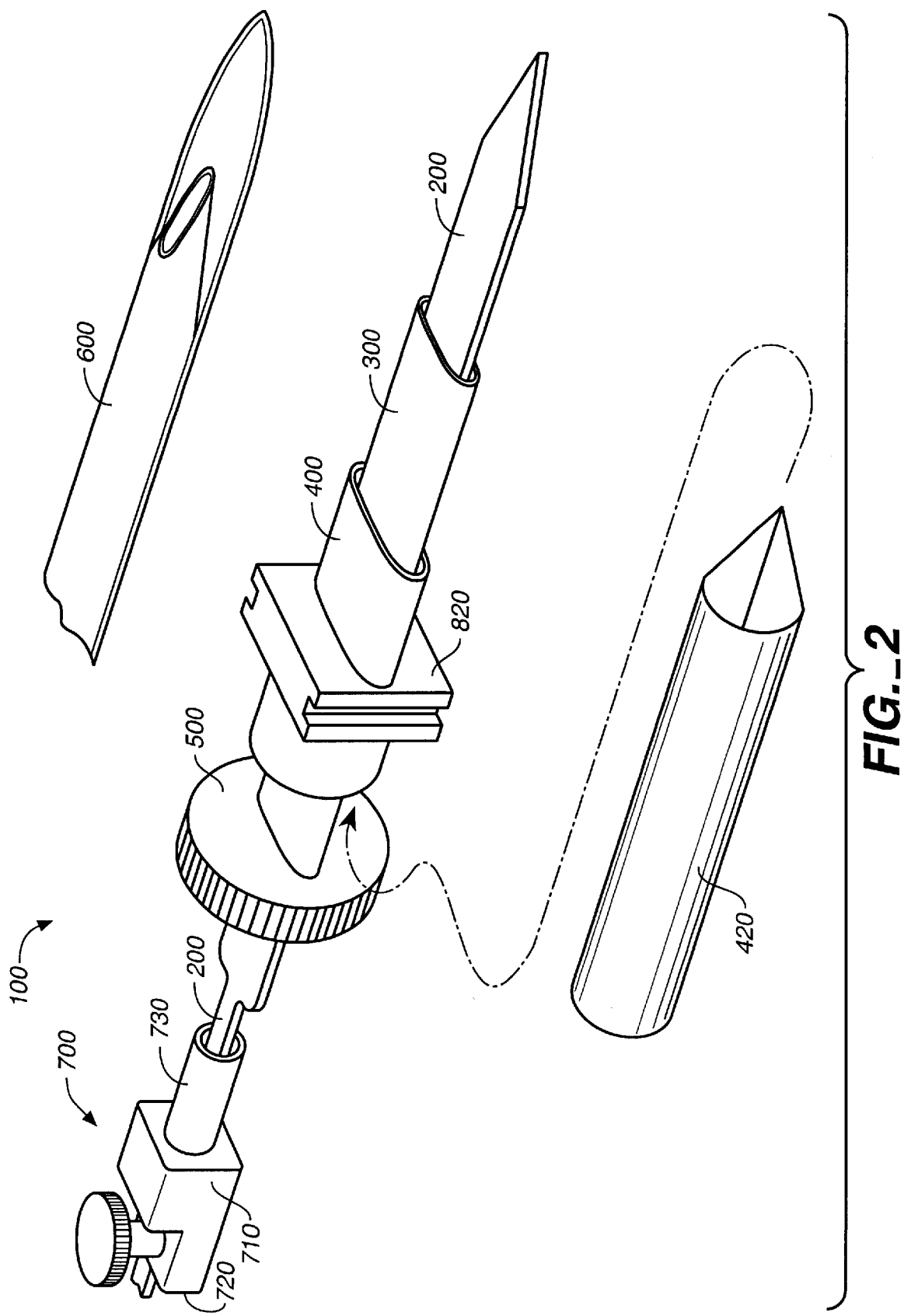
FIG._2

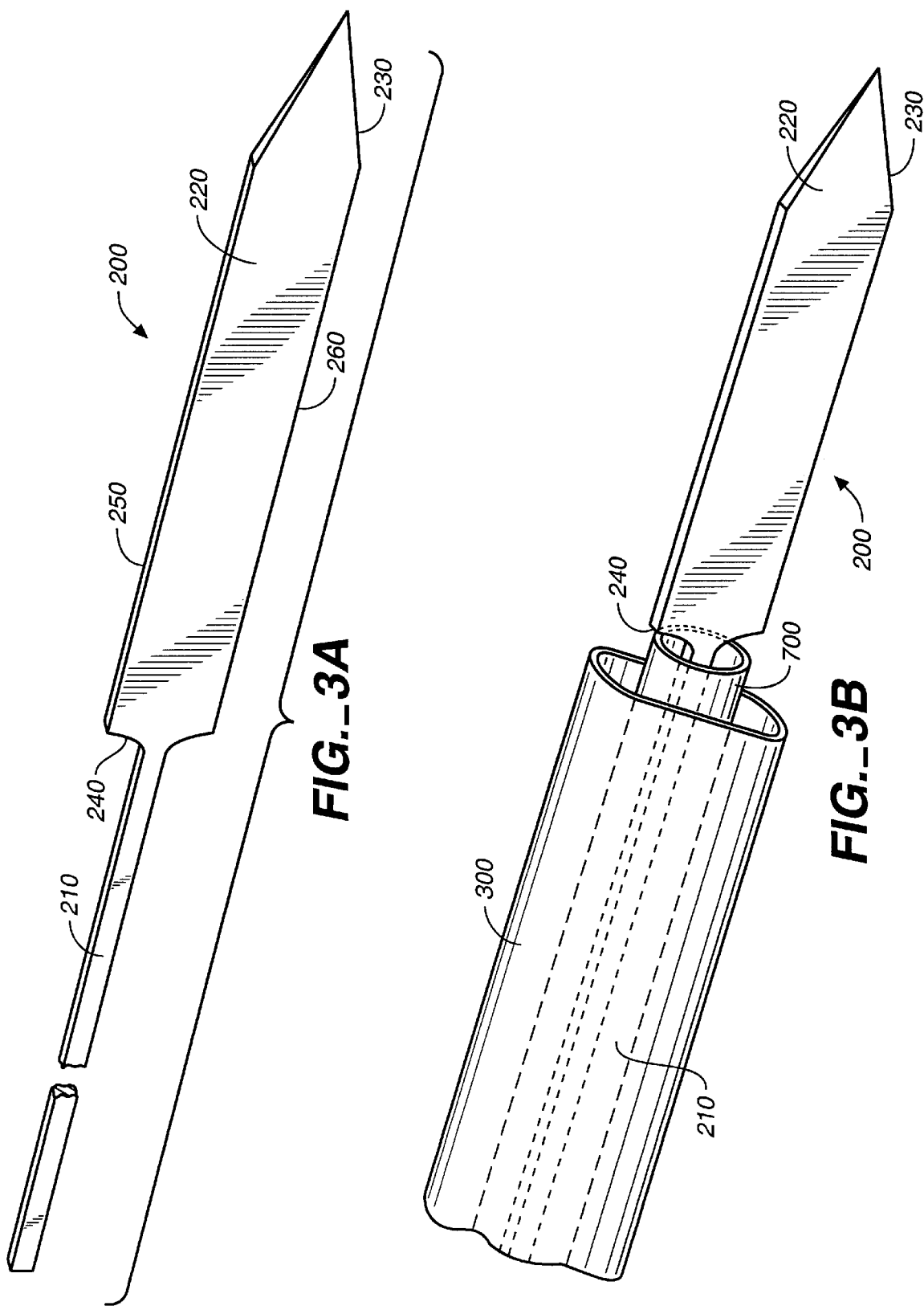

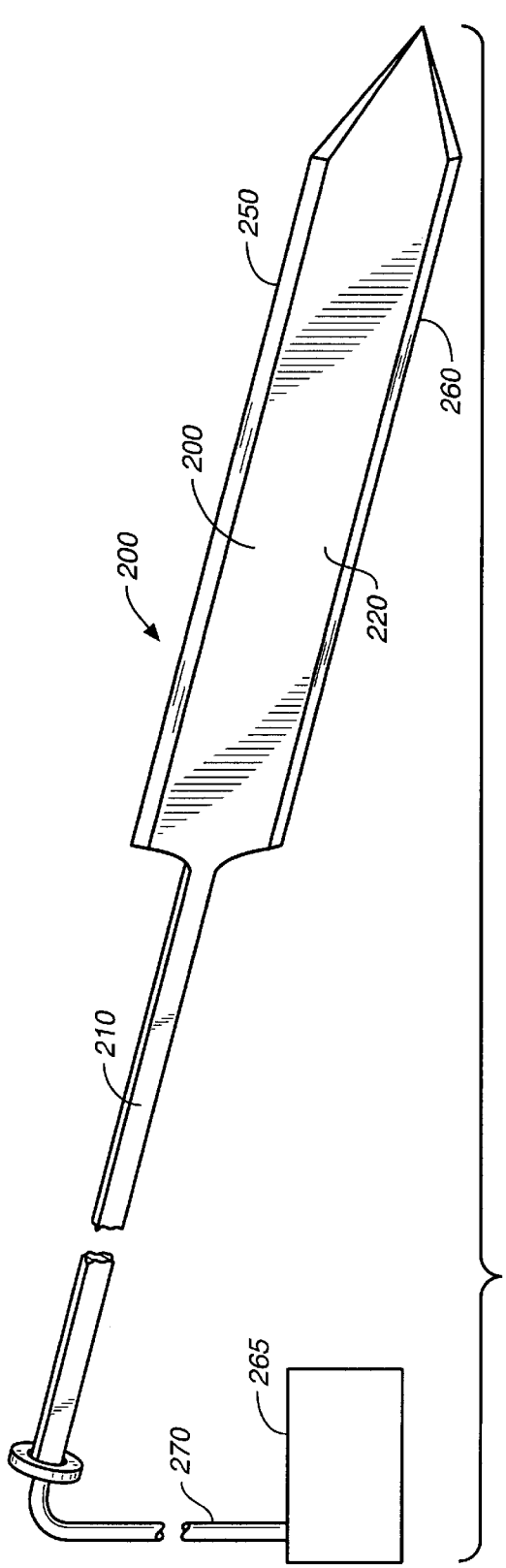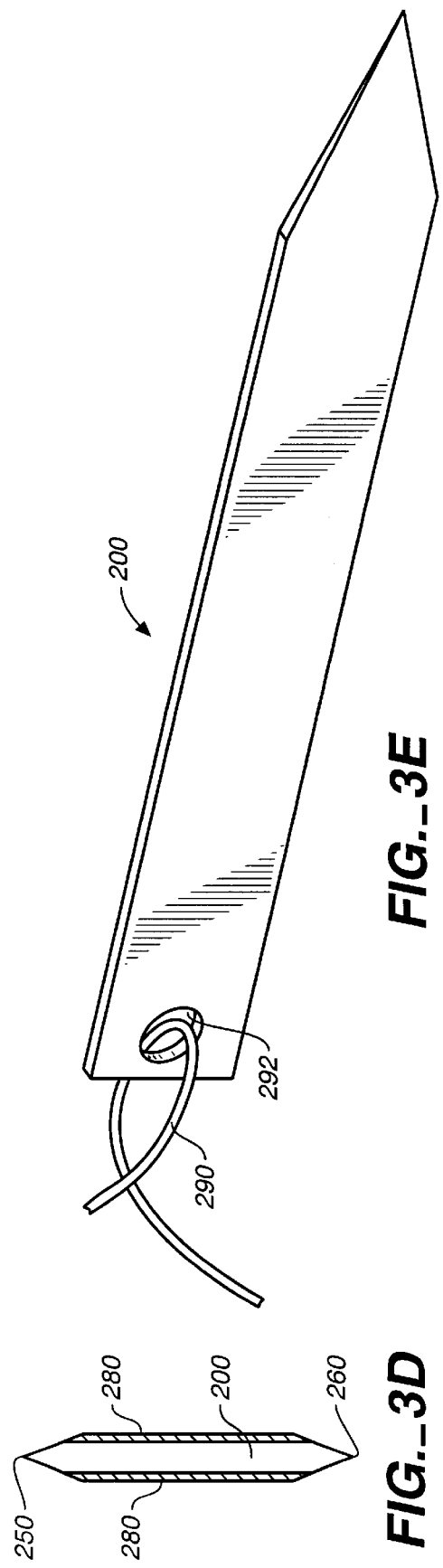
FIG._3C
FIG._3E
FIG._3D

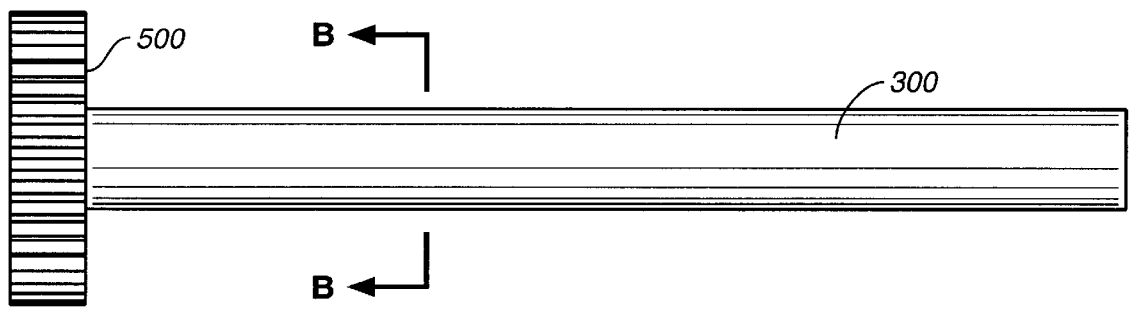
FIG._4A
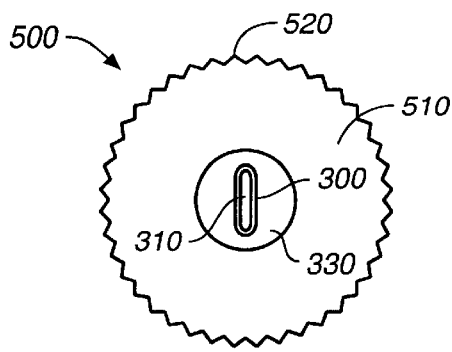
FIG._4B
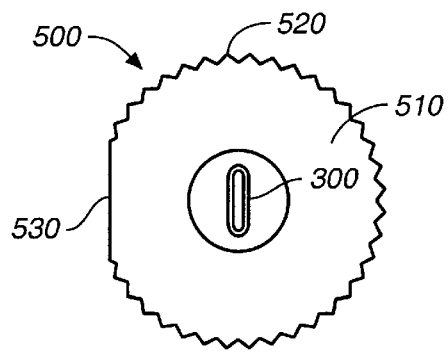
FIG._4C

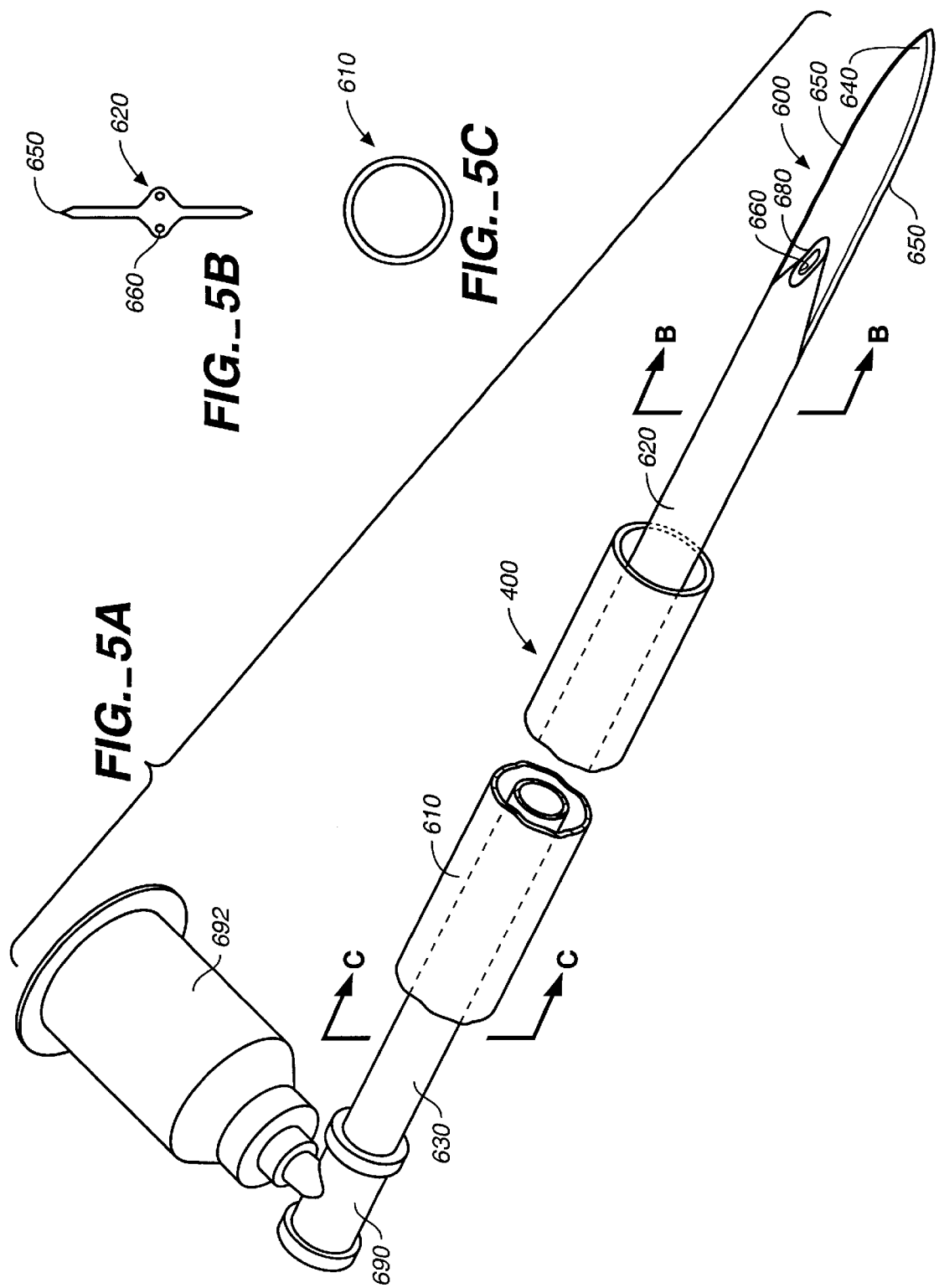

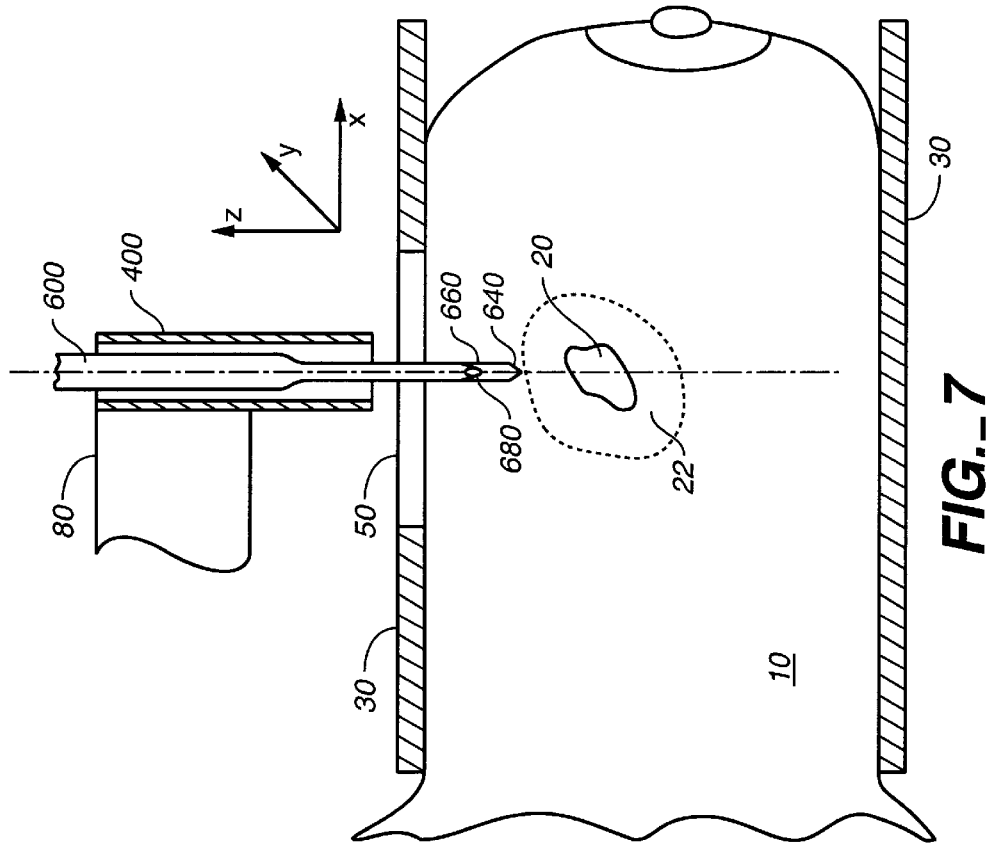
FIG._7
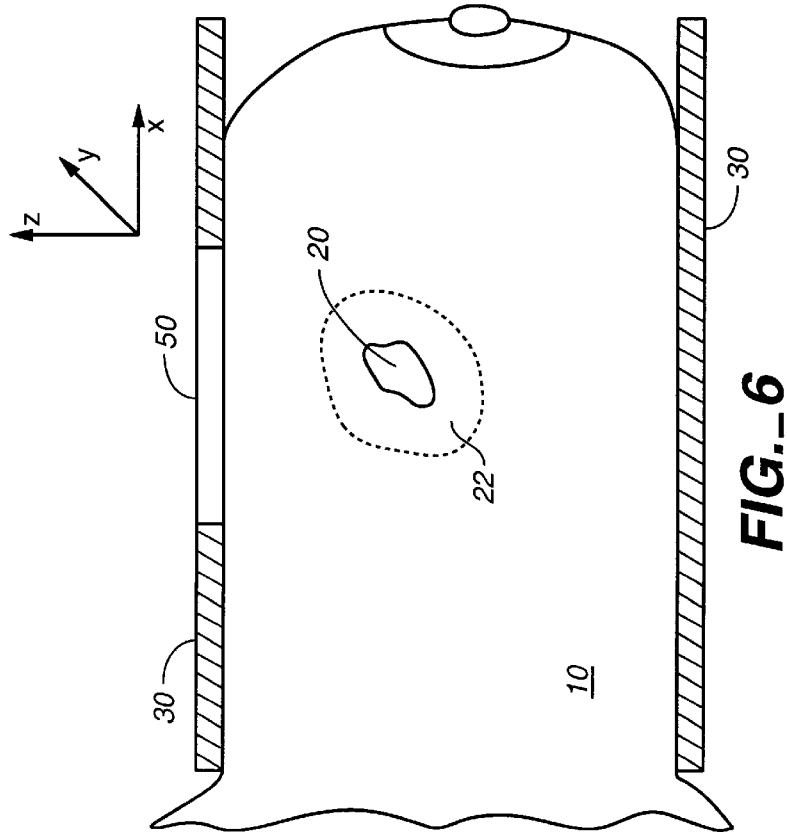
FIG._6

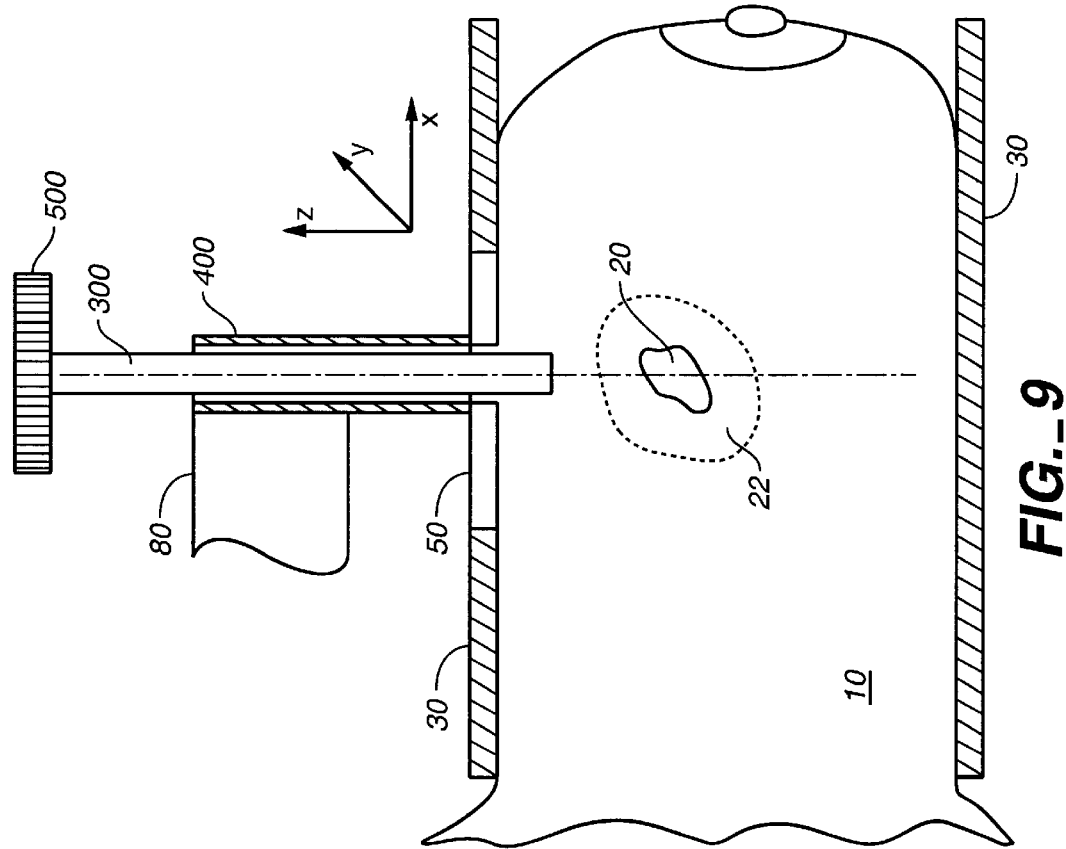
FIG._9
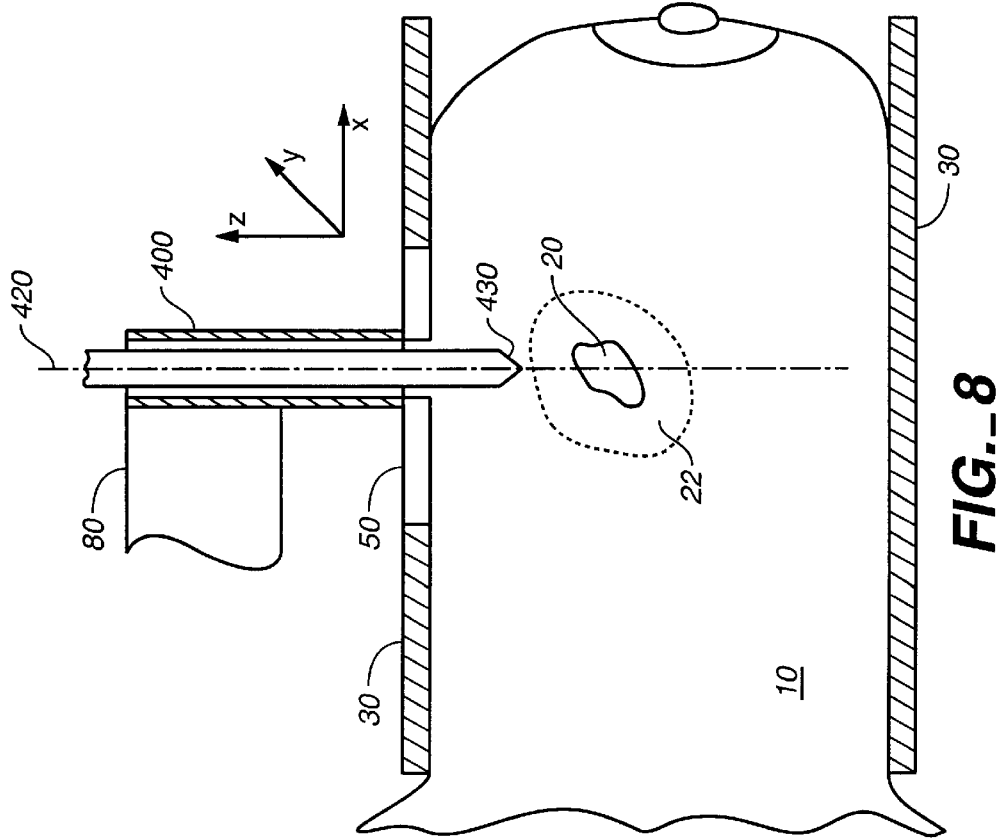
FIG._8

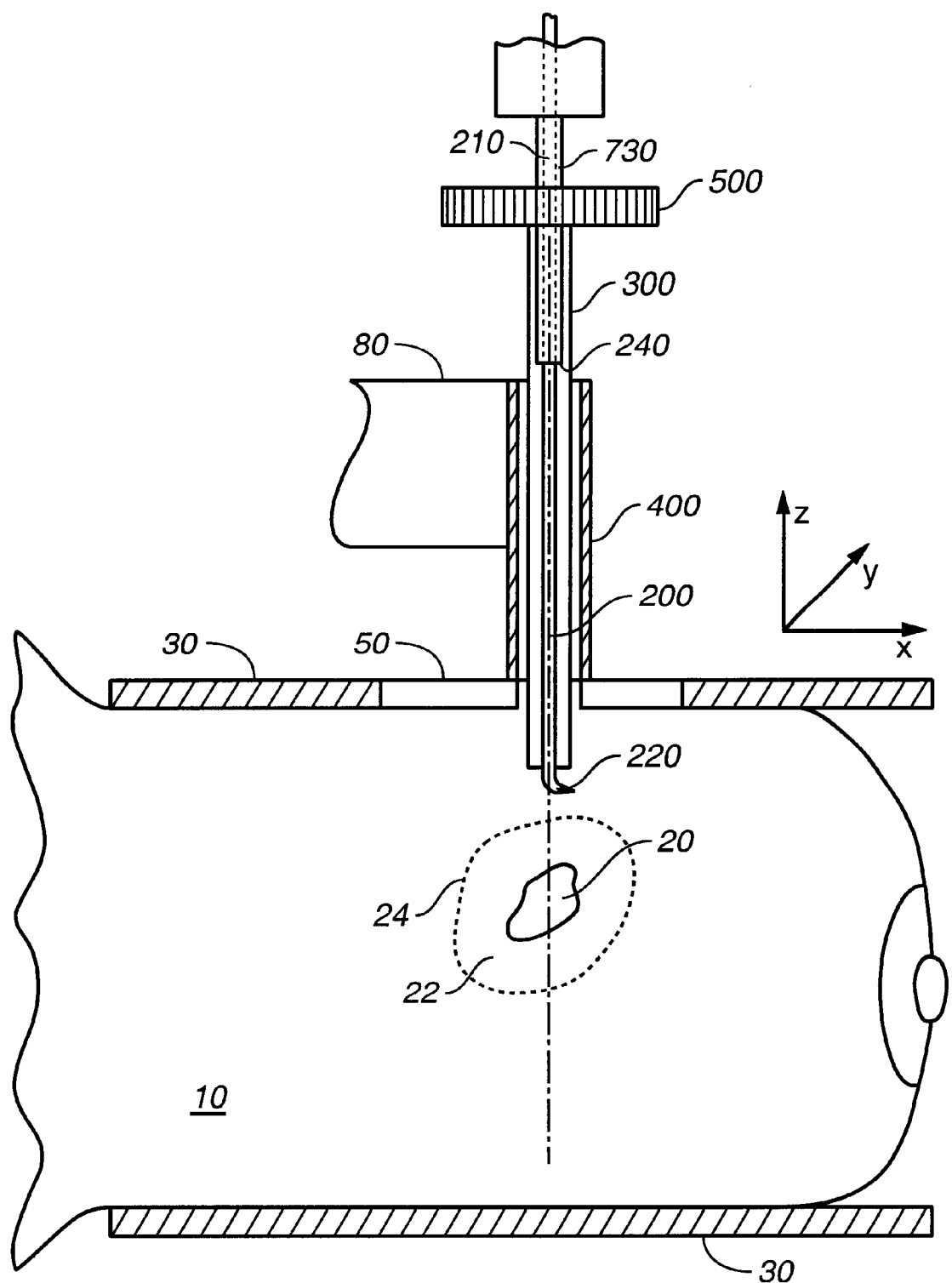
FIG._10

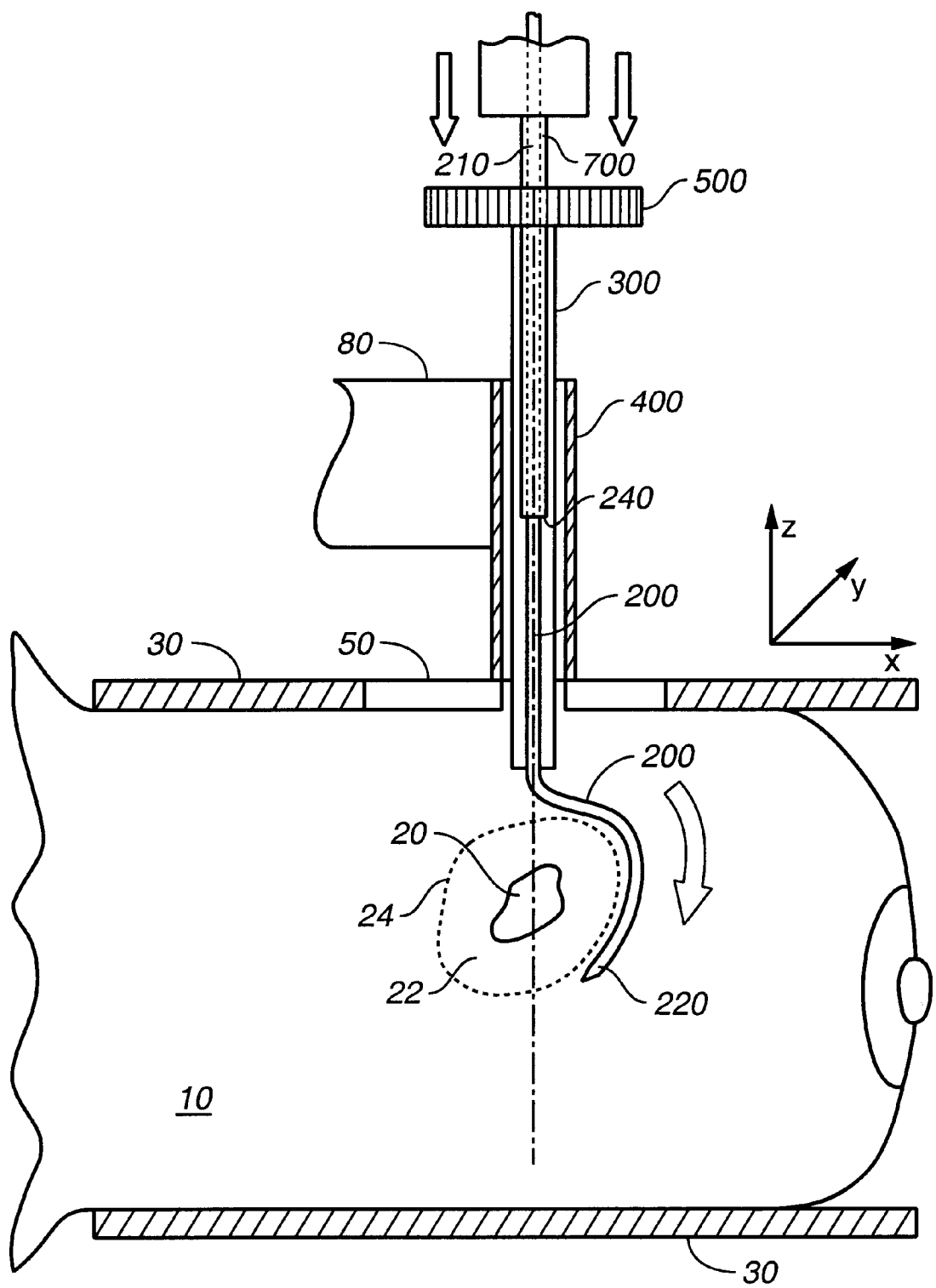
FIG._11

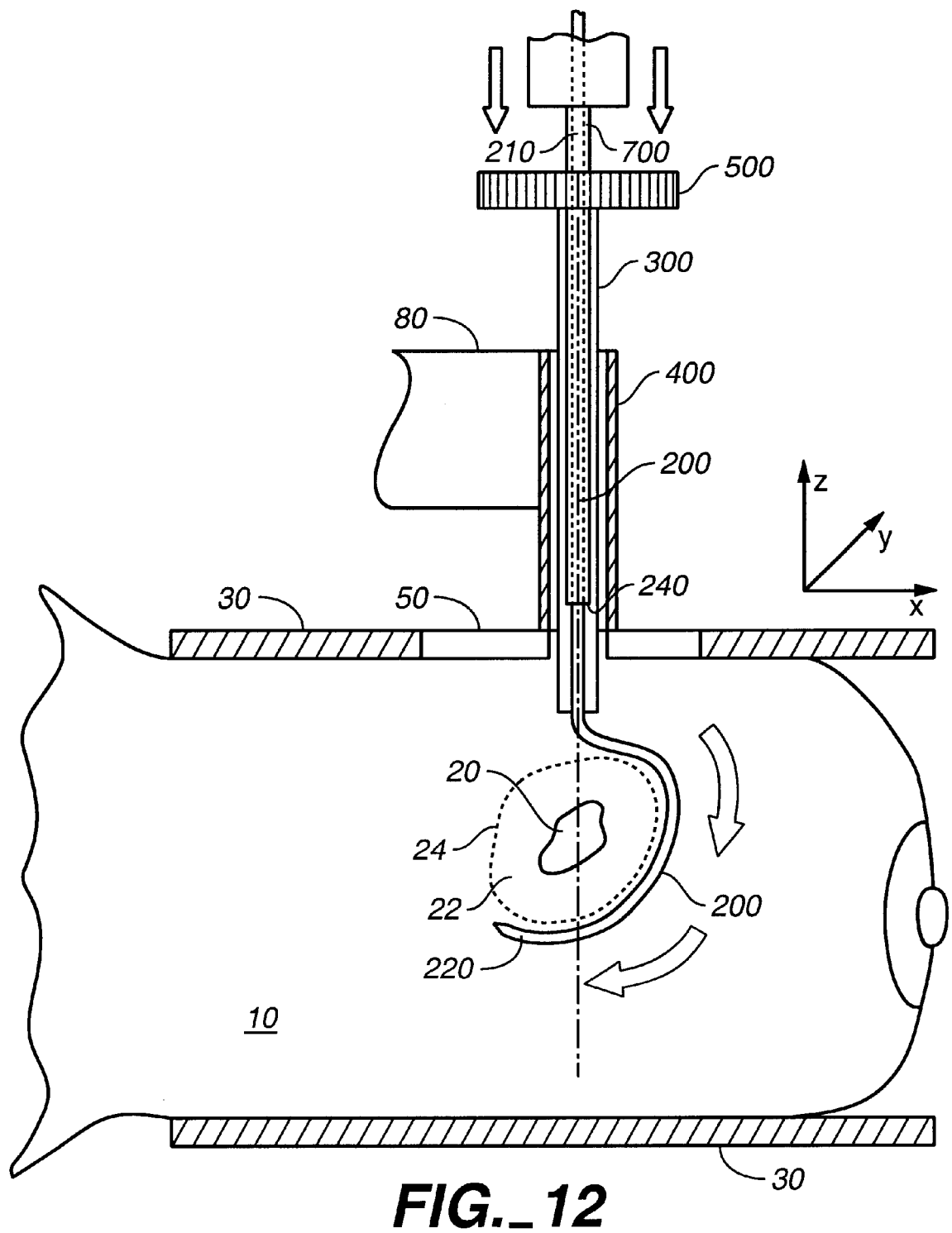
FIG._12

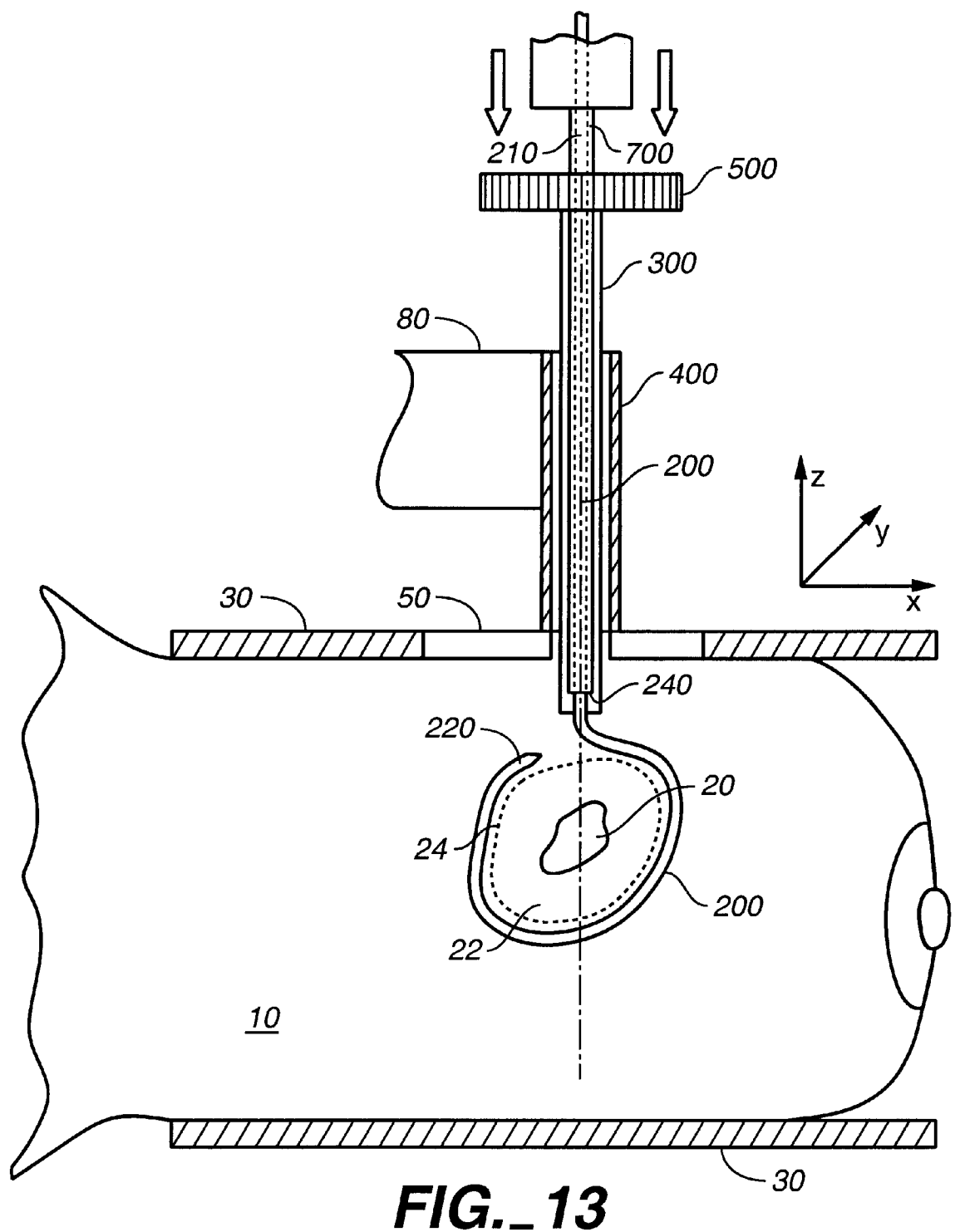
FIG._13

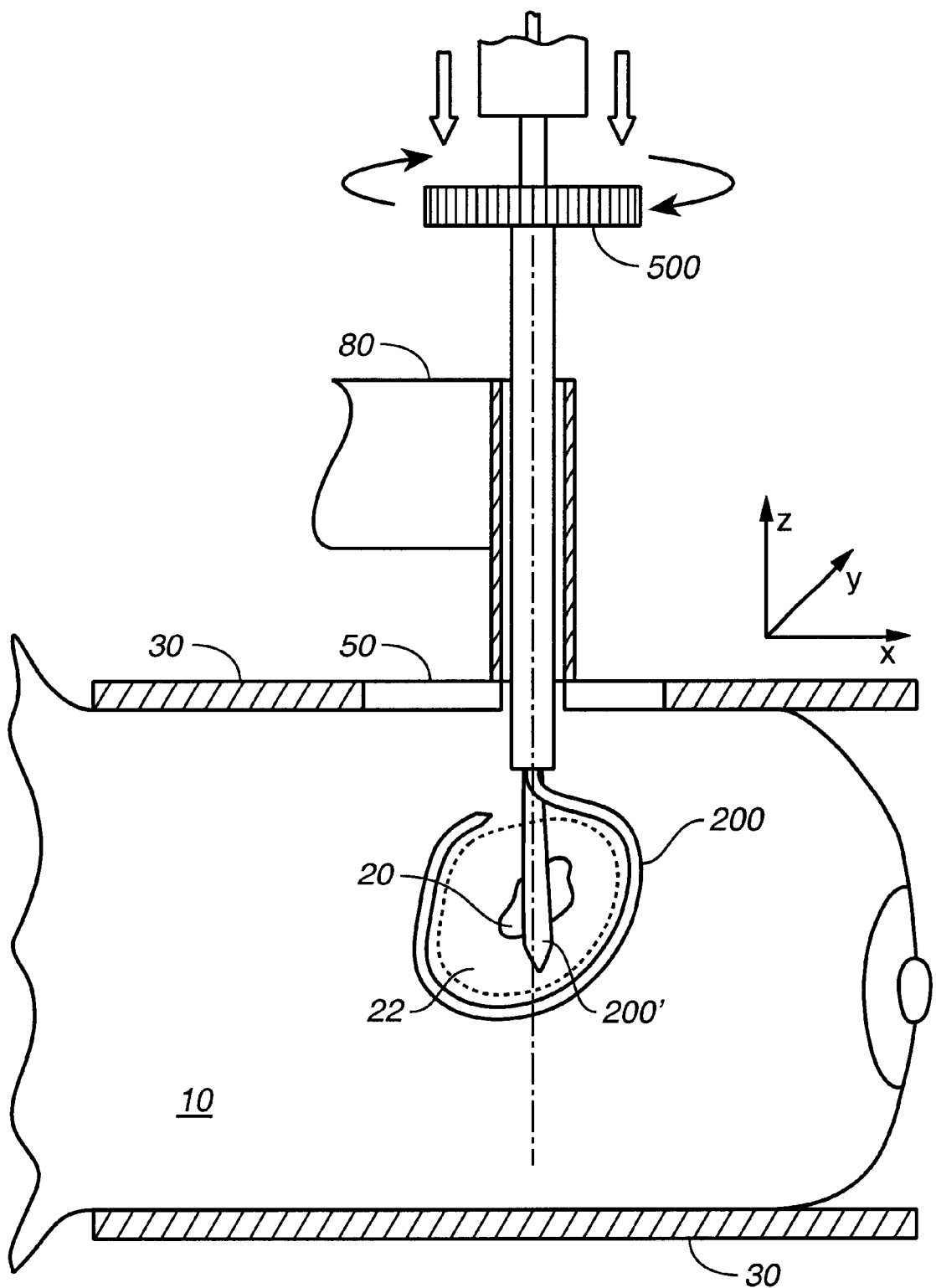
FIG._14

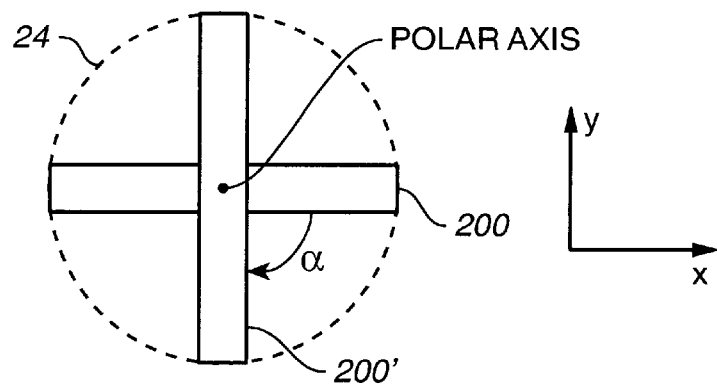
FIG._15
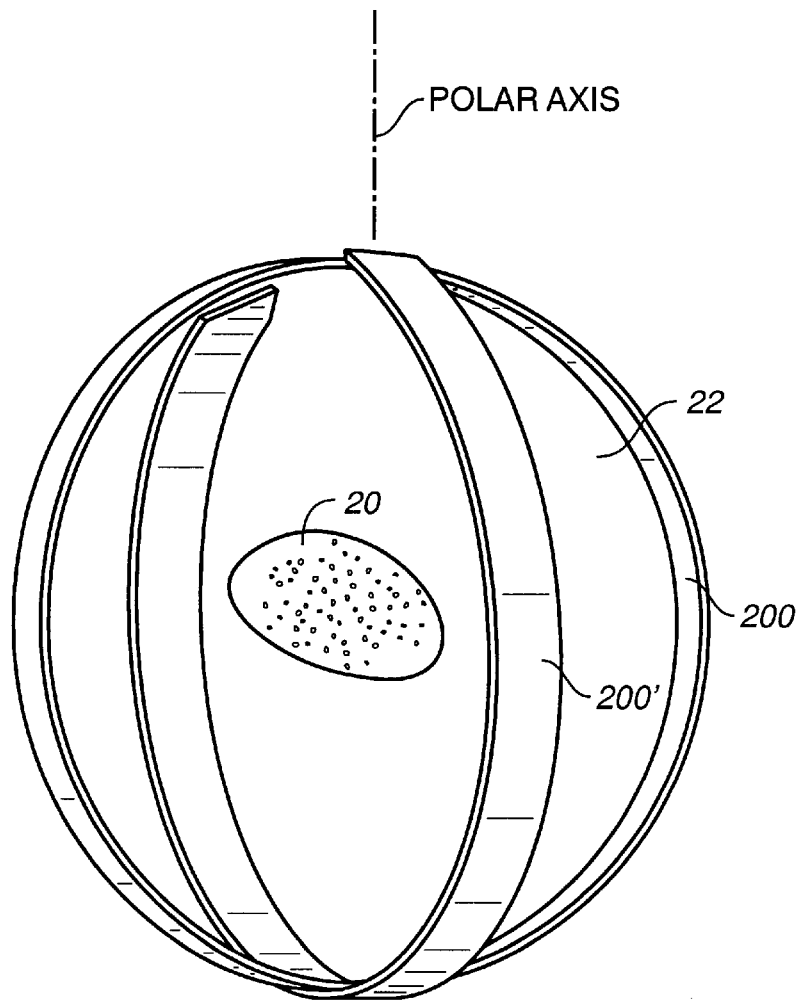
FIG._16

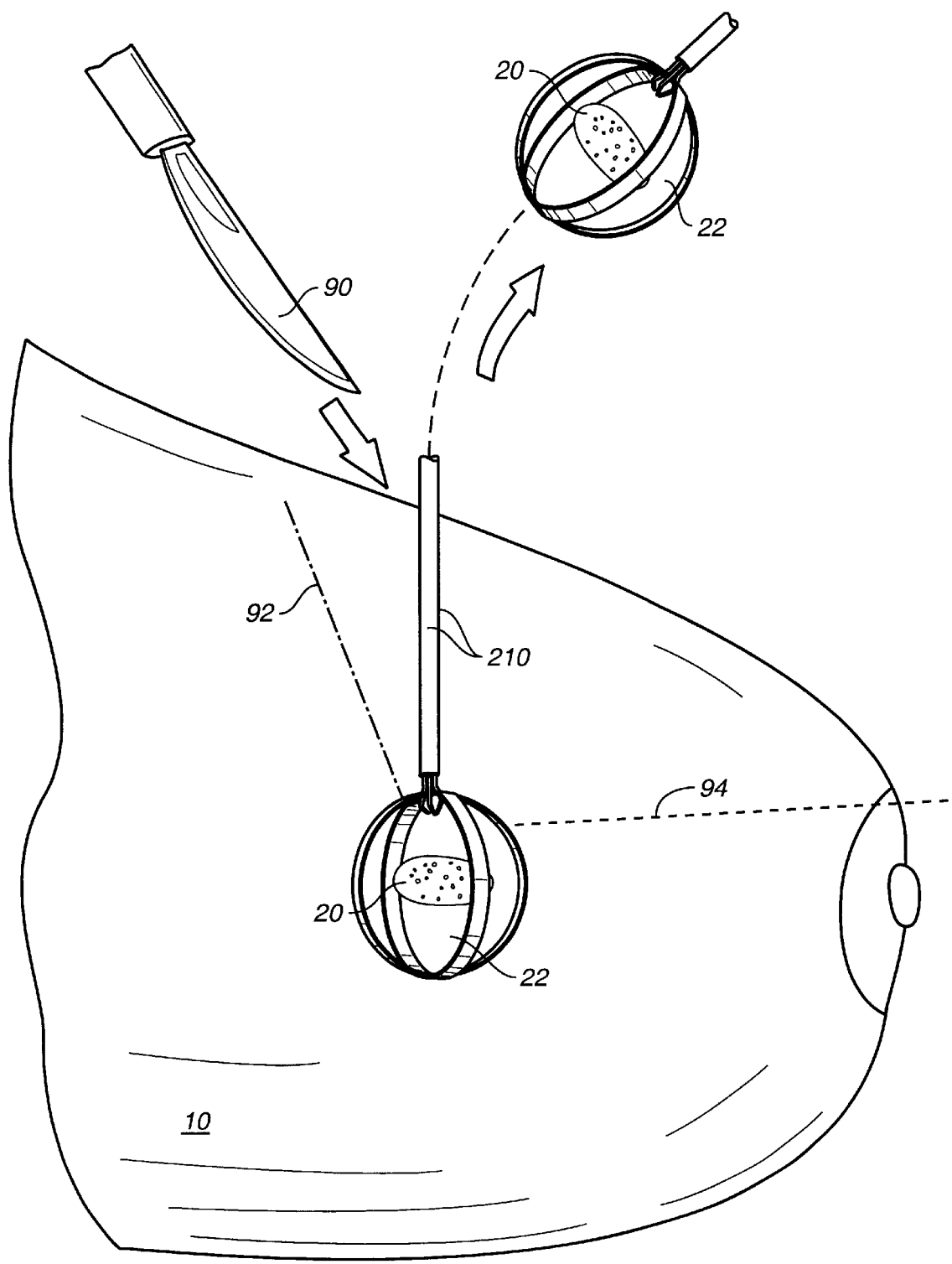
FIG._17

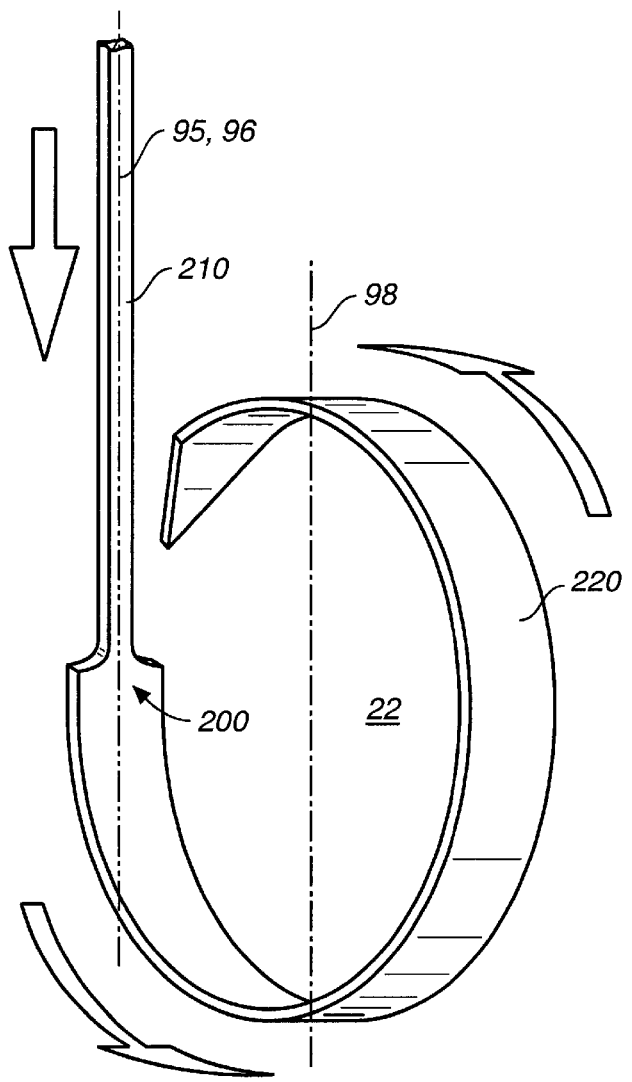
FIG._18A
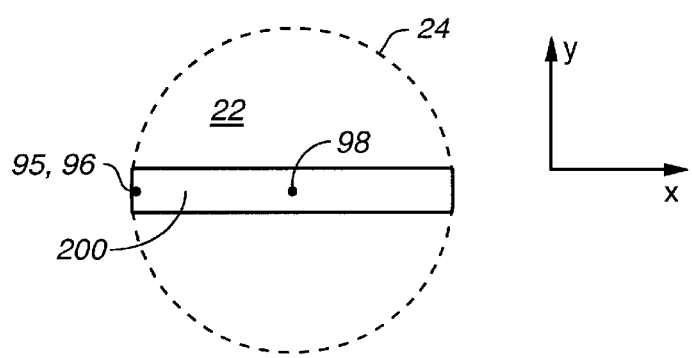
FIG._18B

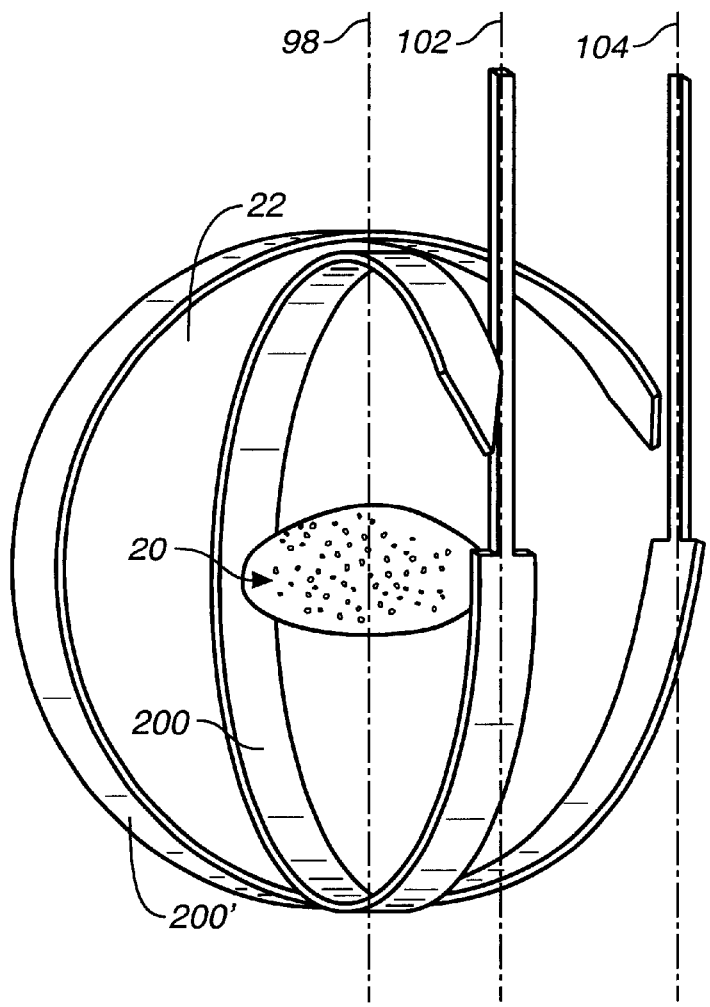
FIG._19A
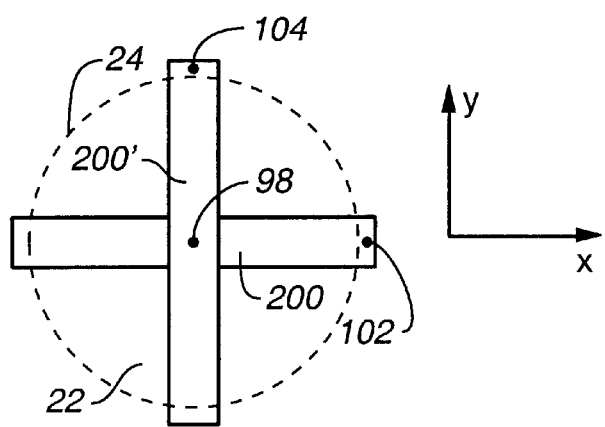
FIG._19B

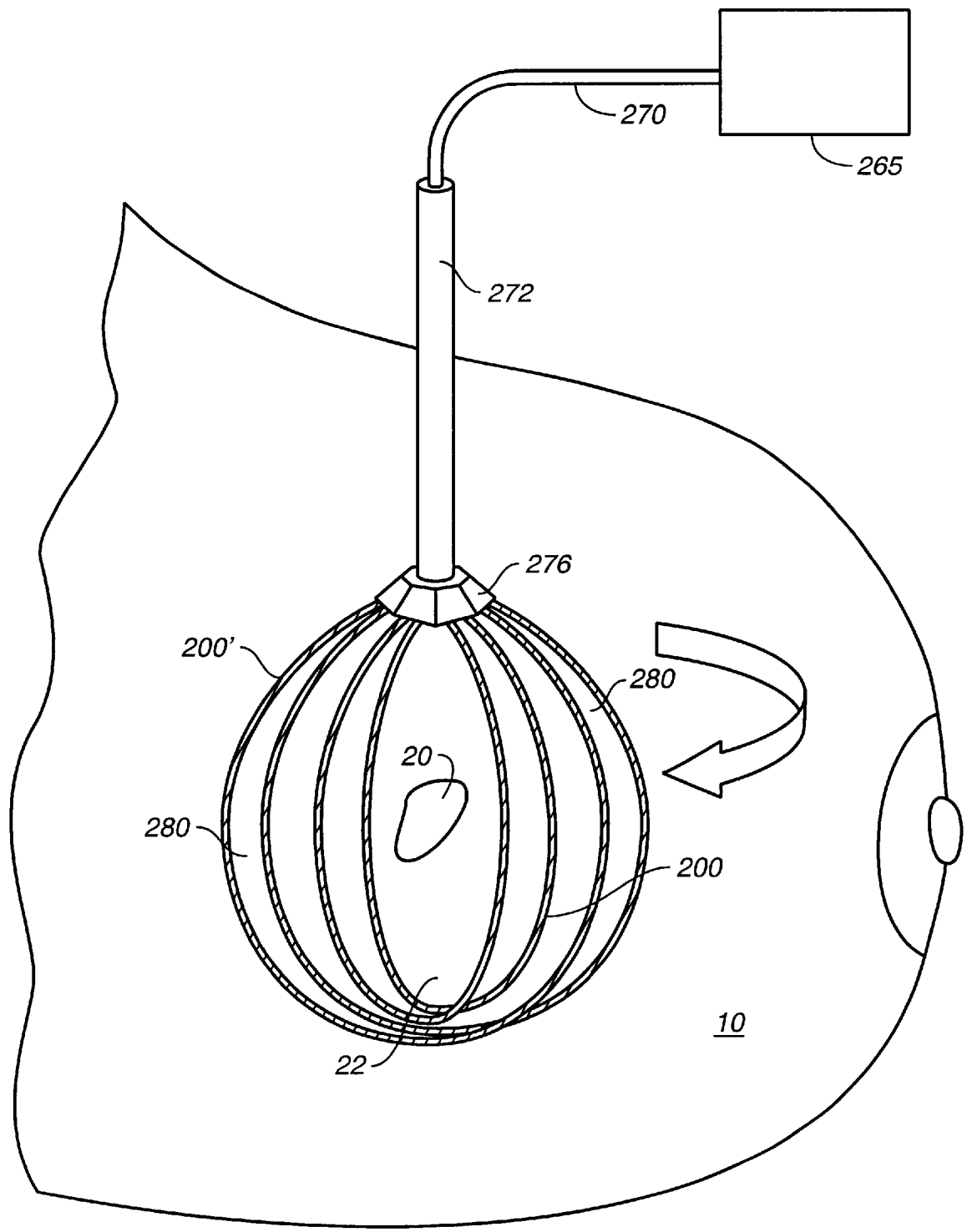
FIG._20

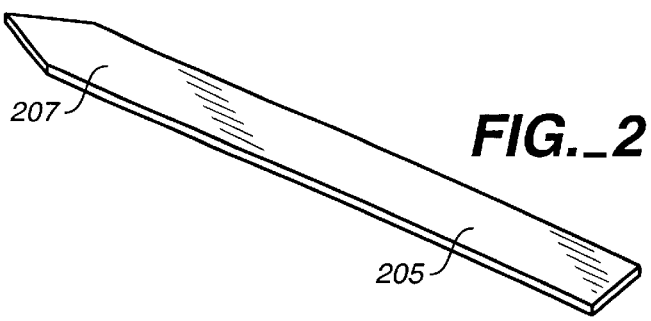
FIG._21A
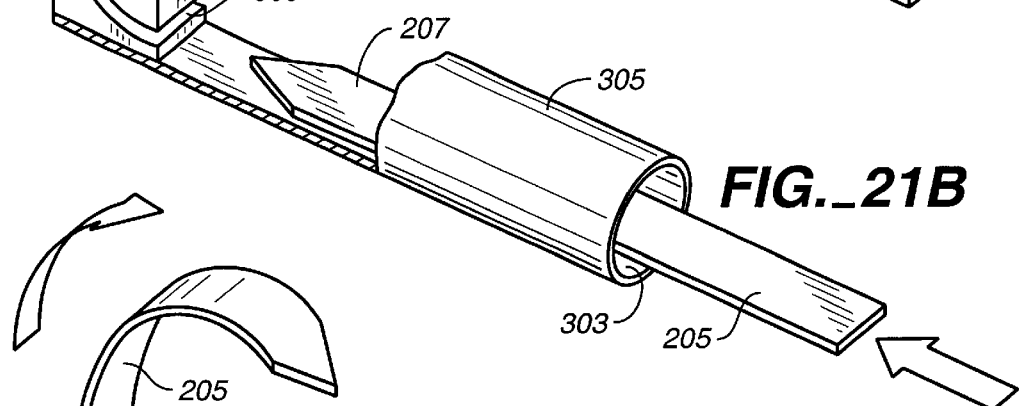
FIG._21B
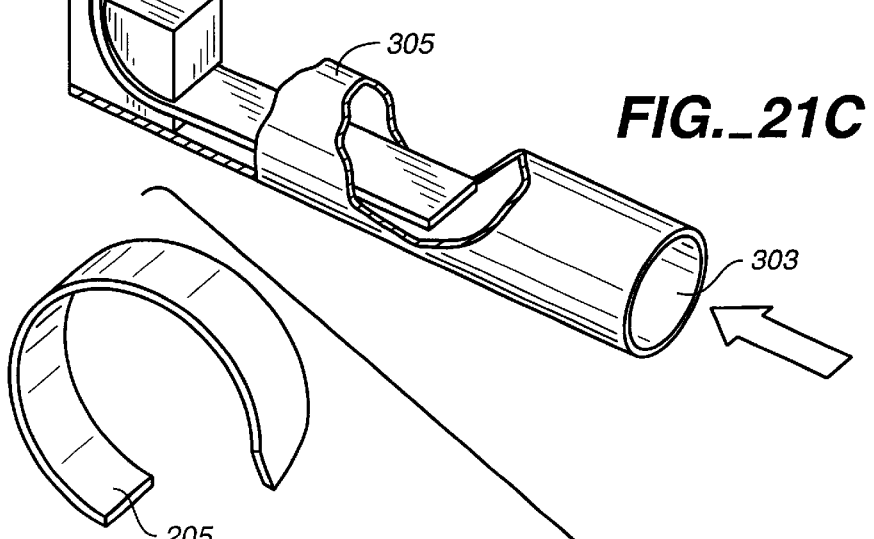
FIG._21C
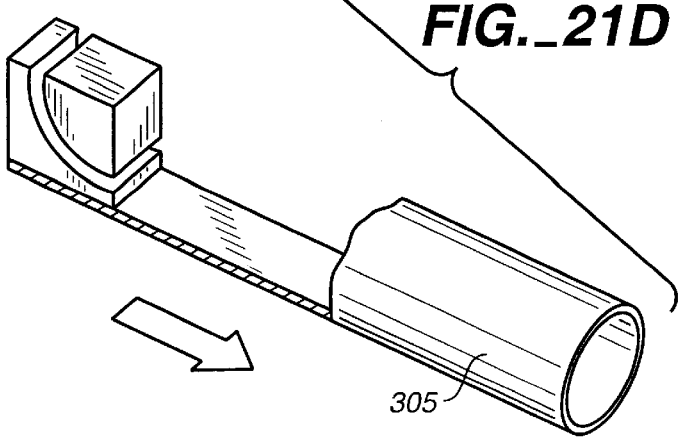
FIG._21D

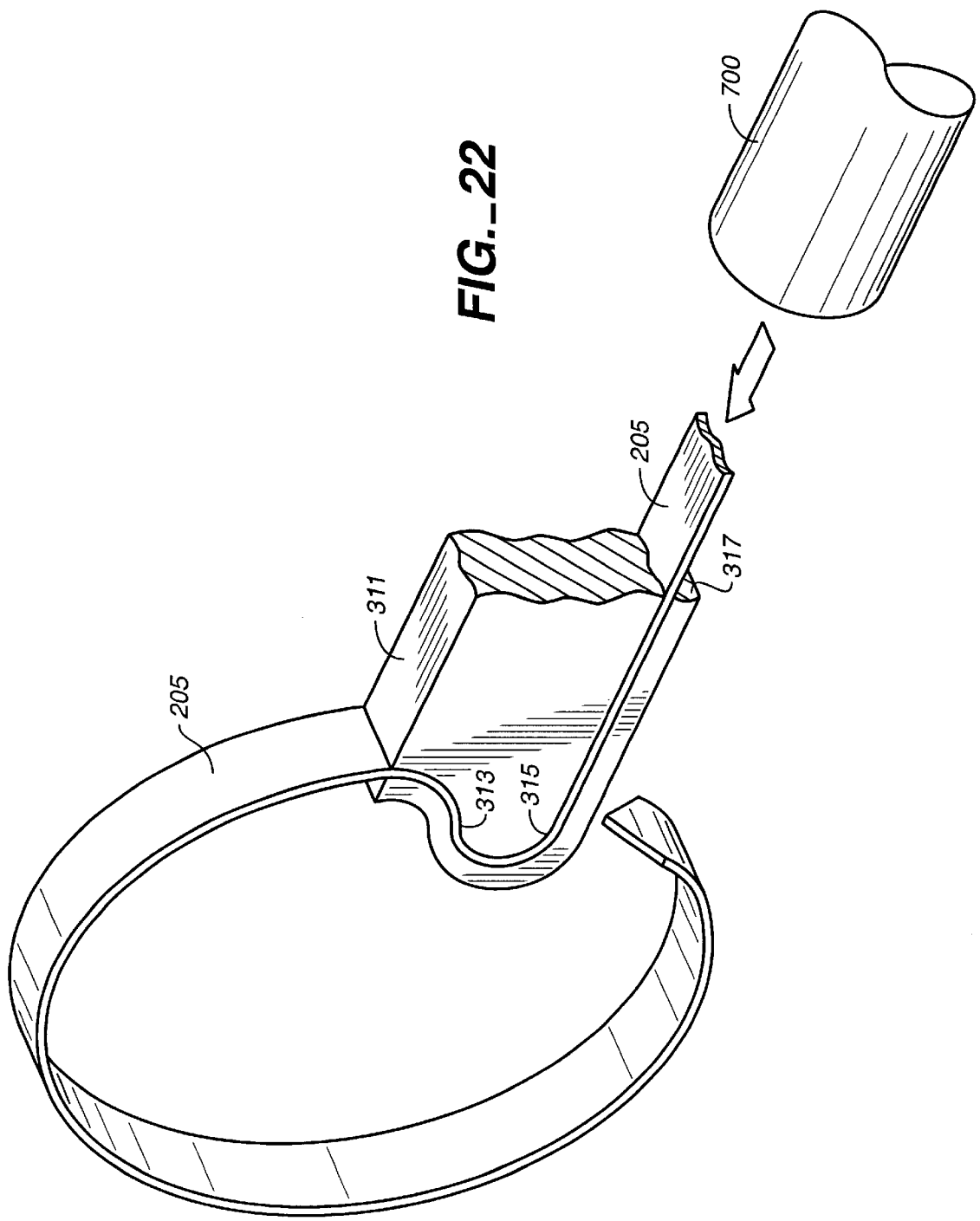
FIG._22

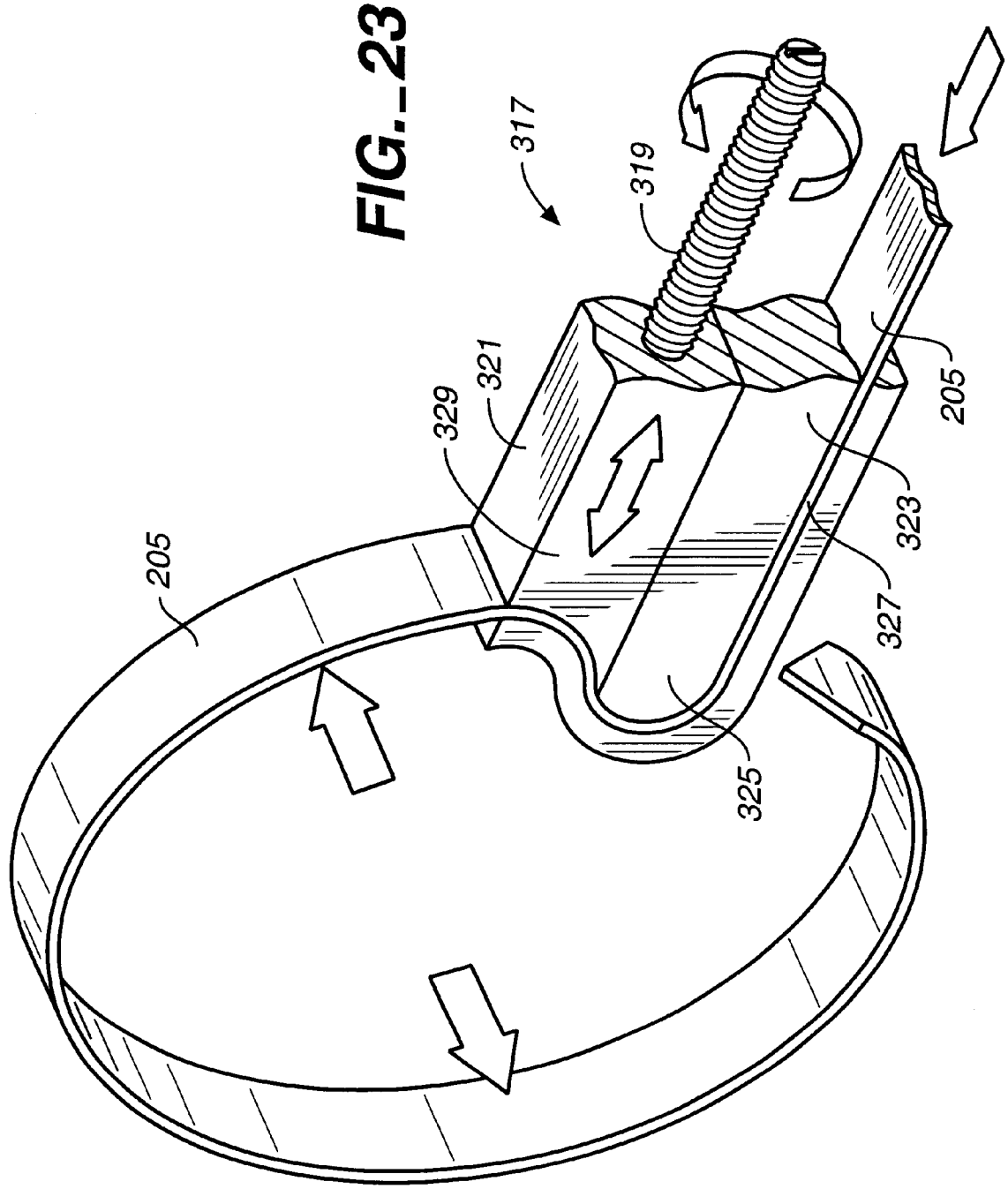

DEVICE FOR ACCURATELY MARKING TISSUE

FIELD OF THE INVENTION

This invention relates generally to tissue localizing devices and methods for their deployment and excision. More particularly, this invention relates to an improved tissue localizing device having the ability to fixedly yet removably bound a tissue volume containing a region of interest, such as a nonpalpable lesion, foreign object, or tumor, without penetrating that tissue volume. This invention also more particularly relates to methods for deploying that device and removing it with an enclosed and intact tissue volume.

BACKGROUND

Despite the advances made in technologies such as medical imaging to assist the physician in early stage diagnosis and treatment of patients with possible atypical tissue such as cancer, it is still often necessary to sample difficult-to-reliably-reach organ or tissue lesions by biopsy to confirm the presence or absence of abnormalities or disease.

One disease for which biopsy is a critical tool is breast cancer. This affliction is responsible for 18% of all cancer deaths in women and is the leading cause of death among women aged 40 to 55.

In the detection and treatment of breast cancer, there are two general classes of biopsy: the minimally invasive percutaneous biopsy and the more invasive surgical, or "open", biopsy.

Percutaneous biopsies include the use of fine needles or larger diameter core needles. They may be used on palpable lesions or under stereotactic x-ray, ultrasonic, or other guidance techniques for nonpalpable lesions and microcalcifications (which are often precursors to metastatic cell growth). In the fine needle biopsy, a physician inserts a small needle directly into the lesion and obtains a few cells with a syringe. Not only does this technique requires multiple samples, but each sample is difficult for the cytologist to analyze as the specimen cells are isolated outside the context of healthy surrounding tissue.

Larger samples may be removed via a core biopsy. This class of procedures is typically performed under stereotactic x-ray guidance in which a needle is inserted into the tissue to drill a core that is removed via vacuum aspiration, etc. Typically four to five samples are taken from the body. Examples of such stereotactic biopsy methods include the MAMMOTOME vacuum aspiration system by Johnson & Johnson of New Brunswick, N.J., the ABBI system by United States Surgical Corporation, Norwalk, Conn., and the SITESELECT system by Imagyn, Inc. of Irvine, Calif.

Open biopsies are advisable when suspicious lumps should be removed in their entirety or when core needle biopsies do not render sufficient information about the nature of the lesion. One such type of open biopsy is the wire localization biopsy.

After multiple mammograms are taken of the breast, the images are analyzed by a computer to determine the location of the suspect lesion in three dimensions. Next, after a local anesthetic is administered, a radiologist inserts a small needle into the breast and passes the needle through the suspect tissue. The radiologist then passes a wire with a hook on its end through the needle and positions the hook so that the end of the wire is distal to the suspect tissue. A final image is taken of the lesion with the accompanying wire in place, and the radiologist marks the film with a grease pencil to indicate the x-ray indicators of a suspicious lesion that should be removed. The wire is left in the tissue and the patient is taken to the operating room, sometimes hours later, where the suspect tissue is removed by a surgeon. The sample is sent to a radiologist to determine, via an x-ray examination, if the sample contains the indicators such as microcalcifications and if the sample size and border are adequate to confirm the removal of all suspicious tissue.

Examples of such wire markers are well known in the art. See, e.g., the following patents, each of which is incorporated herein by reference: U.S. Pat. No. 5,158,084 to Ghiatas, U.S. Pat. No. 5,409,004 to Sloan, U.S. Pat. No. 5,059,197 to Urie et al., U.S. Pat. No. 5,197,482 to Rank, U.S. Pat. No. 5,221,269 to Miller et al., and U.S. Pat. No. 4,592,356 to Gutierrez. Other devices such as that described in U.S. Pat. No. 5,989,265 to Bouquet De La Joliniere et al. and U.S. Pat. No. 5,709,697 to Ratcliff et al., each incorporated herein by reference, are directed to similar devices.

Despite the advantages of wire localization techniques to locate the suspect tissue for the surgeon, they have a number of severe limitations.

Such wires are often inaccurately placed and they cannot be removed except by surgical excision. For these reasons, the radiologist must mark the x-ray film or prepare notations providing instructions to the surgeon on how to find the lesion as a backup to confirm the proper location of the needle.

Because the distal tip of the wire might have been placed anywhere from the very center of the lesion to quite some distance away from the lesion, the surgeon must guide a scalpel along the wire and rely upon the skill of the radiologist and the marked x-ray film in the excision procedure. Even if the wire has been properly placed in the lesion and the x-ray film clearly shows the lesion boundary or margin, the surgeon often cannot see the tip of the wire (given the surrounding tissue) so she must remove a larger portion of tissue than is necessary to ensure proper excision.

If the lesion is not found at the end of the wire, the surgeon ends up cutting or removing non-afflicted tissue without removing the lesion. Also, if the tip of the wire penetrates the lesion, the surgeon may sever the lesion in cutting through the tissue along the wire to reach its end. In the latter case, a re-excision may be necessary to remove the entire lesion. Over twenty-five percent of wire localization procedures require re-excision. Post-excision re-imaging is almost always performed prior to closing the surgical field to ensure that the targeted tissue volume containing the suspect lesion is removed.

When marking lesions in the breast, two paddles are typically used to compress and stabilize the breast for placement of the wire. Upon release of the breast from compression, the wire marker can dislodge or migrate to another position away from the suspect tissue. It may also migrate while the patient awaits surgery. In addition, the fact that the breast is in an uncompressed state for the excision procedure renders a different view of the lesion with respect to the healthy tissue.

Various tissue localization systems have been developed to minimize inadvertent migration of the wire by configuring the wire with a bend or hook, such as Ghiatas et al., discussed above, U.S. Pat. No. 5,011,473 to Gattuma, and the MAMMALOK needle/wire localizer sold by Mitek Surgical Products, Inc., Dedham, Mass. Even if a wire does not migrate after placement, the surgeon cannot determine the shortest path to the lesion; rather, the surgeon must always follow the wire, which is rarely the more cosmetically desirable path to the lesion (such as a circumareolar approach).

Because the distal tip of the wire is often placed in the center of the suspect tissue, a problem known as "track seeding" can occur in which possible cancerous or precancerous cells are disturbed by the wire and are distributed to unaffected tissue during the procedure.

Aside from the above concerns, the use of a localization wire marker presents logistical problems. After placement, the wire protrudes from the body. It is almost always necessary for the patient to proceed with the surgical removal of the lesion immediately after wire placement to minimize the chance of infection, wire breakage or disturbance, etc. However, delays between placement of the wire and eventual excision often can exceed several hours.

What is needed is a tissue locating device that may be accurately yet removably placed into a region of tissue to surround a volume of tissue that contains a suspect region, preferably without penetrating that volume to disturb it. Such a device should reliably define the border of the volume of tissue to be removed without the risk of self- or inadvertent migration. The device should also provide a surface against which the surgeon may reliably cut when excising the tissue. Furthermore, a need remains to improve the interaction between the radiologist and surgeon, eliminate the need for post-excision x-rays and re-excision, reduce the overall time for the procedure, and allow a surgeon to select the shortest or most cosmetically desirable path to the suspect tissue.

SUMMARY OF THE INVENTION

This invention is a tissue localizing device, system, and method for its use.

The tissue localizing device includes a locator element adapted to penetrate tissue so that at least a portion of the locator element defines a tissue border along a first path. This path may include the distalmost portion of the tissue volume. This border in turn defines a volume of tissue for subsequent excision and contains a target region that may be a lesion, foreign object, one or more microcalcifications, or a palpable or nonpalpable mass. This tissue volume is substantially bounded but preferably not penetrated by the locator element. The path the locator element is adapted to follow preferably forms a loop in the tissue having a diameter of at least one centimeter. When deployed, manipulation of a proximal portion of the locator element results in a corresponding direct or proportional manipulation of the tissue volume it bounds.

Preferably the locator element is a partially radiopaque ribbon with one or more optional cutting surfaces. The locator element also preferably exhibits shape memory characteristics. Alternatively, the locator element may be plastically deformed to take an arcuate or curvilinear shape during deployment through a die.

A shoulder portion may be included in the locator element defining a boundary between a preferably more flexible, less rigid proximal portion having a smaller cross-sectional area and a stiffer, more rigid distal portion having a larger cross sectional area compared to that of the proximal portion.

This device may contain a second locator element adapted to penetrate tissue so that at least a portion of it further defines the tissue border along a second path. Again, the target region is substantially bounded but preferably not penetrated by the second locator element. Each of the first and second locator elements may be deployed through a deployment tube having a lumen in which the locator elements are slideably disposed and a distal end through which they may exit into the tissue. The second locator element may be adapted to deploy into the tissue so that it defines a second plane that is not parallel to a first plane defined by the first locator element. These planes may be angularly displaced about a common axis about ninety or forty-five degrees with respect to one another.

The locator elements are adapted to be substantially aligned when deployed with a central axis of the tissue volume they bound or with a tangential axis of that volume.

An optional suture, flexible wire, or cable may be affixed to a proximal end of the locator element to extend through the tissue volume and outside the skin surface when deployed in the body.

This invention is also a tissue localization system which includes a tissue cutting element positionable within a lumen of a driver tube, a trocar positionable within the driver tube lumen, a locator element deployment tube positionable within the driver tube lumen, and at least one locator element positionable within the deployment tube. The cutting element may additionally comprise at least one lumen or tubular member having a distal end disposed along its length.

The locator element is adapted to penetrate tissue so that at least a portion of the locator element defines a tissue border along a first path. The tissue border defines a volume of tissue for subsequent excision along the border, and contains a target region that is substantially bounded by the locator element.

An orientation element also may be attached to the locator element deployment tube, which may be rotatable in fixed angular increments and/or may be infinitely rotatably variable.

A source of energy, such as electrical (RF, etc.), thermal, acoustic, mechanical, or other may be connected to the locator element. The locator element may also be at least partially electrically insulated by a coating of insulative material on one or more sides of the element. This insulative material may have a low coefficient of friction for ease of entry into the tissue if desired.

The locator element deployment tube may comprise a distal end having a locator element cold forming die that may be adapted to plastically deform the locator element into an arcuate shape. The die may include a reverse curve and a positive curve for shaping the locator element, and it may also comprise an axially adjustable upper portion connected to a lower portion.

This invention is also a method for fixedly placing a removable locator element in tissue. This method is accomplished by penetrating through tissue at a first site to create a port or a pathway for accessing a targeted tissue volume to be excised, inserting a deployment tube containing a locator element slideably contained within a lumen of the tube through the port to a position adjacent the targeted tissue volume, and advancing a locator element through a distal end of the tube and penetrating tissue so that at least a portion of the locator element defines a tissue border along a first path. The tissue border will define a volume of tissue for subsequent excision along the tissue border. The tissue volume will contain a target region that is substantially bounded but not penetrated by the locator element.

Alternatively, the invention is a method for excising a volume of tissue which comprises advancing a locator element through tissue to define a tissue border of the volume of tissue to be excised, and cutting tissue substantially along a surface of the locator element opposite a surface of the locator element disposed immediately adjacent the tissue volume.

The locator element may be proximally withdrawn from the tissue after it is advanced to define the tissue border for eventual re-advancement through the distal end of the deployment tube or complete removal from the body.

The locator element may be placed under x-ray guidance, stereotactic x-ray guidance, ultrasonic guidance, magnetic resonance imaging guidance, and the like.

A second and even third or more locator element may also be advanced through the distal end of the deployment tube to penetrate tissue so that at least a portion thereof further defines the tissue border along a second and even third path. The second path and the third path may be non-parallel to the first path occupied by the first locator element, and may be angularly displaced with respect thereto approximately thirty degrees, forty-five degrees, ninety degrees, or at any other angle or angles the radiologist so desires.

This method also includes the step of excising the tissue volume defined by the one or more locator elements. This may be accomplished by surgically accessing the locator element and cutting tissue substantially along a surface of the locator element opposite a surface of the locator element disposed immediately adjacent the tissue volume. Preferably, the device is palpable when in position around the tissue volume. Tissue may be penetrated through any accession path to the tissue volume as the surgeon sees fit. For instance, the surgeon may cut down along the locator element deployment tube, or, when the device is disposed in breast tissue, circumareolarly.

Furthermore, excision may be accomplished or complimented by at least partially energizing the locator element with electrical energy such as RF energy, mechanical energy, thermal energy, vibrational or acoustic energy, and the like. Rotation of the locator element or elements through an angular displacement to facilitate cutting through tissue to remove the tissue volume is contemplated.

BRIEF DESCRIPTION OF THE DRAWINGS

FIG. 1A depicts a prior art wire localization technique.

FIG. 1B depicts a further prior art wire localization technique.

FIG. 2 shows a tissue localization system according to the present invention.

FIG. 3A shows one embodiment of a tissue locating element according to the present invention.

FIG. 3B shows the tissue locating element of FIG. 3A together with a deployment tube and pusher assembly tube.

FIG. 3C shows another embodiment of a tissue locating element according to the present invention that is connected to an external energy source.

FIG. 3D is a cross-sectional view of the tissue locating element of FIG. 3C.

FIG. 3E is yet another embodiment of a tissue locating element according to the present invention connected to a flexible wire or suture.

FIGS. 4A–4C show various views of a deployment tube and attached orientation element according to the present invention.

FIGS. 5A–5C show various views of a tissue cutting element of the present invention disposed in a cannula for making an initial incision into tissue prior to deployment of the tissue locator element, complete with optional syringe and hub.

FIG. 6 shows breast tissue containing a lesion and surrounding tissue volume placed between two compression paddles.

FIG. 7 shows the breast tissue and lesion of FIG. 6 penetrated by a blade extending distally from a cannula.

FIG. 8 shows the breast tissue and lesion of FIG. 6 with the blade removed and a trocar advanced into the tissue through the cannula to open up a pathway for accessing the lesion.

FIG. 9 shows the breast tissue and lesion of FIG. 6 with the trocar removed and a deployment tube and orientation element deployed in the cannula.

FIG. 10 shows the breast tissue and lesion of FIG. 6 with a locator element being advanced distally into the tissue by a pusher.

FIG. 11 shows the apparatus of FIG. 10 with the locator element advancing along a border of the tissue volume containing the lesion.

FIG. 12 shows the apparatus of FIG. 10 with the locator element continuing its advance along a border of the tissue volume containing the lesion to enclose a distal portion of the tissue volume.

FIG. 13 shows the apparatus of FIG. 10 with the locator element substantially deployed along a majority of a border of the tissue volume containing the lesion.

FIG. 14 shows the apparatus of FIG. 10 with an additional locator element partially deployed along a second path defining a border of the tissue volume containing the lesion at an angle to the first locator element.

FIG. 15 is a top view of the apparatus of FIG. 14 with the second locator element fully deployed.

FIG. 16 is a perspective view of the apparatus of FIG. 14 with the second locator element fully deployed, demonstrating a polar deployment configuration.

FIG. 17 shows various paths the surgeon may take to excise the tissue volume substantially bounded but preferably not penetrated by the locator elements.

FIGS. 18A–18B show a perspective and top view, respectively, of a locator element of the present invention deployed in a tangential configuration.

FIGS. 19A–19B show a perspective and top view, respectively, of two locator elements of the present invention deployed in a tangential configuration.

FIG. 20 shows two locator elements of the present invention connected to a source of energy.

FIGS. 21A–21D show a cold-forming process for shaping and deploying a locator element of the present invention with a deployment tube having a die.

FIG. 22 shows another embodiment of a cold-forming die according to the present invention.

FIG. 23 shows yet another embodiment of an adjustable cold-forming die of the present invention having reverse and positive die cavity curves.

DETAILED DESCRIPTION OF THE INVENTION

The invention described herein is appropriate for a wide range of applications for marking a specific volume of tissue for excision or other purposes. Although the description below is largely in the context of marking a nonpalpable lesion in breast tissue and its subsequent excision, the invention is not so limited. For instance, the invention described herein can be used to mark tissue in a variety of locations in the body, such as the liver, the lungs, muscle tissue, or other tissue or organs where the advantages of the invention can be utilized. It may also be used to mark a foreign object in tissue or body cavities as well, such as a bullet or the like. Accordingly, the invention and method for its use as described and claimed below is not limited to the marking and removal of lesions from breast tissue.

FIGS. 1A and 1B depict the current state-of-the-art tissue location methodology and equipment for nonpalpable breast lesions. In particular, FIG. 1A depicts a cross-section of breast tissue 10 having the lesion 20 to be marked for later removal disposed between two compression paddles 30 (shown in cross-section). A window 50 lies in the upper paddle 30 for accessing the lesion, which is surrounded by tissue volume 22. A localization wire 40 is shown placed in the lesion. The wire 40 depicted herein is "J"-shaped, and it may have a barb or hook on its distal tip to assist in anchoring the wire 40 in the breast tissue 10.

Note that in FIG. 1A, breast tissue 10 contains a typically nonpalpable lesion 20 or suspect tissue which is targeted for removal. Lesion 20 may contain precancerous or cancerous cells or it may contain one or more microcalcifications, which are often precursors to metastatic cell growth. Microcalcifications typically appear in clusters.

When removing these lesions 20, a primary concern is that a large enough volume 22 of tissue is removed so that all of the suspect tissue is enclosed therein. The border or perimeter of this volume 22, when properly sized, is colloquially called a "clean margin". If the pathologist finds suspect tissue on or near the border of volume 22, a "dirty margin" is present and additional tissue must be removed from the body along the previous tissue volume border until the pathologist is comfortable that all the suspect tissue has been removed. It is generally the goal, then, to remove the volume 22 of tissue completely containing within its borders the suspect tissue or lesion 20.

A radiologist performs this procedure under local anesthesia, typically under x-ray guidance. In the following discussion, we assume the wire localization technique shown in FIGS. 1A and 1B as well as the method of the present invention is performed under stereotactic x-ray guidance.

Normally the breast 10 containing the lesion 20 to be removed is placed between two compression paddles 30 to stabilize it for imaging and placement of wire 40. Identification of the lesion 20 under this technique is based on measurements of the position of the lesion on two images of the breast taken from different angles (typically +15 degrees and −15 degrees), called a stereo pair. The lesion is preferably centered below window 50.

Next, a computer maps the breast tissue by generating a set of coordinates corresponding to the targeted lesion 20 and a portion of the tissue 10 surrounding the lesion. Under stereotactic x-ray guidance, coordinates are generated in three dimensions (x, y and z). The z coordinate typically denotes to the depth of the lesion from the skin in a direction perpendicular to the surfaces of paddles 30, while the x and y coordinates define a horizontal plane parallel to the plates 30. This mapping procedure pinpoints the location of the lesion 20 as defined by the radiologist. The paddles are adjusted so that lesion 20 is centered in the x-y plane below window 50 along a vertical (or z) axis.

A small needle is next inserted into the tissue through window 50 in the upper compression plate 30 and moved towards the suspect tissue. This needle (not shown) acts as a deployment tube for localization wire 40.

The radiologist then passes localization wire 40 through the needle so that the distal end 60 is positioned in or adjacent lesion 20. Typically, wire 40 will have a barbed or hooked distal end 60 or may take on "J" shape as shown in FIG. 1A.

A follow-up x-ray is taken of the lesion with wire 40 in place, and the radiologist will mark the x-ray image to indicate the location of lesion 20.

The radiologist next decompresses the tissue and transfers the patient to surgery for removal of lesion 20. It should be clear from this discussion that it is difficult at best to accurately determine the proper depth (along the z-axis) to which the surgeon should cut to safely and satisfactorily excise the lesion.

FIG. 1B shows a less common technique in which a second wire 70 is used to mark the lesion 20. Here, the coordinates of the lesion are determined and the wires 40 and 70 are deployed on either side of the lesion, defining the margin along an x or y direction. The radiologist then marks the approximate lesion location on the x-ray as described before. The margins in the other two dimensions must again be approximated; the margins along the vertical or "z" axis are once again particularly difficult to determine with any degree of accuracy.

The technique shown in FIG. 1B, called "bracketing" or "goalposting", is often used in a second localization attempt when the radiologist was unsuccessful in marking the lesion in a prior attempt.

As previously described, these techniques require post-excision re-imaging (and often re-excision and re-imaging) to ensure that the entire lesion is removed before the wound can be closed and the patient can be sent home.

Turning now to the present invention, FIG. 2 shows one embodiment of a tissue localization system 100 that overcomes the deficiencies of current systems and methods.

System 100 typically comprises the following subsystems or components: a tissue locator element 200, locator element deployment tube 300, a driver tube 400, locator element orientation element or clock wheel 500, tissue cutting element or blade 600, trocar 420, and pusher assembly 700.

System 100 is versatile. For instance, a stereotactic guide unit 80 may be connected to the driver tube 400 or some other component as shown in FIGS. 7–9. Guide unit 80 interfaces with a stereotactic x-ray system to guide system 100 to the proper coordinates as discussed above. System 100 may be delivered via a variety of imaging modalities, including a mammography unit (either freehand or under stereotactic assistance), on a stereotactic table, under ultrasound or magnetic resonance imaging guidance, etc.

System 100 may alternatively or additionally be connected to a device such as a Fisher Table to provide a stable platform from which the system can be used to mark tissue under x-ray guidance. An alternative driver positioning member or clevis 820 may also be connected to a custom made vise or a commercially available driver, which in turn may be connected to a Fisher Table or other platform. This enables system 100 to be used with existing commercially available platforms and drivers, ensuring ease of use, low cost, and maximum versatility.

In general, after tissue 10 is mapped and centered between paddles 30, blade 600, which is slideably disposed in a lumen of driver tube or cannula 400, is deployed through a distal end of cannula 400 into the breast tissue to the vicinity of the volume of tissue containing the lesion to be removed. Blade or cutting element 600 may contain one or more tubular portions along its length, each having a lumen through which lubricant or an anesthetic may be administered as is discussed later.

A proximal end of blade 600 may be disposed in a lumen of tubular pusher element 730, which is part of pusher assembly 700. As shown in FIG. 2, pusher assembly 700 may also include a clamping ferrule or similar element 710 having a lumen for slideably receiving a proximal portion of blade 600 and, more importantly, locator element 200. A thumbscrew or similar securing member 720 is provided to fix a proximal section of blade 600 or locator element within the pusher assembly ferrule 710. Pusher assembly 700 may also be affixed to the aforementioned platforms or drivers in a variety of configurations; the arrangement described herein is merely exemplary.

After advancing the cutting element 600 through the tissue 10 to reach the vicinity of the tissue volume of interest, the blade 600 is withdrawn and driver tube or cannula 400 together with trocar 420 are inserted into the proximity of tissue 10. Cannula 400 may follow trocar 420 or may advance into the tissue simultaneously with trocar 420. Preferably, driver tube 400 is advanced to the skin surface but does not penetrate (or just slightly penetrates) tissue 10. This further opens up a passageway or port in the tissue for deployment of additional components of system 100.

After the trocar reaches the desired location near the tissue volume, it is proximally withdrawn from driver tube 400, which is left in the tissue, and a preferably oval deployment or delivery tube 300 is inserted through the lumen of driver tube 400 so that its distal end is disposed in the region of the tissue volume to be excised.

The radiologist next advances a locator element 200, which is preferably radiopaque, through the distal end of the tube 300 lumen to penetrate tissue and occupy the tissue volume boundary. Locator element 200 is preferably designed to take on an arcuate or curvilinear shape when extended through the tube 300 distal end, such that as it penetrates tissue it follows a planar and preferably arcuate or curvilinear path to create a physical border around the majority of the perimeter of the targeted tissue volume, preferably without penetrating it. The locator element 200 is designed to remain fixedly yet removably in place once deployed in tissue 10 as will be described later in greater detail.

Delivery tube 300, driver tube 400, and any other component of system 100 may then be removed, leaving only the locator element fixedly in place in the targeted tissue. Preferably, but not necessarily, the locator element is long enough so that a reduced profile proximal end (or alternatively an attached suture or the like) extends proximally through the surface of the skin.

The patient may then either delay the excision procedure as desired or as dictated by the surgeon's schedule, or she may be transferred to surgery for excision of the marked volume.

During the excision process, the surgeon cuts along the wire or the proximal portion of the locator element 200, following it to the vicinity of the tissue volume. The surgeon excises the tissue volume without invading the volume interior by cutting around the surface of the locator element opposite the locator element surface directly adjacent the tissue volume. The surgeon may also access the locator element 200 by any number of approaches not necessarily along the proximal portion of element 200, such as circumareolarly or via some other more direct or cosmetically acceptable approach as she sees fit.

Alternatively, prior to removing the remaining components of system 100 from the tissue, one or more additional locator elements may be deployed through delivery tube 300 into the tissue at an angle with respect to and about a longitudinal axis of the first locator element. This may be accomplished by the use of a clock wheel or orientation element 500 which may be rotated to orient the locator element or elements to a predetermined angle. Once oriented, the additional locator element or elements are deployed into the tissue in the same manner as the first locator element. These additional elements further define the same tissue volume along a different but similar arcuate path. The particular angular orientation of each deployed locator element with respect to each other may be arranged (e.g., at forty-five or ninety degrees) so that the spatial orientation and location of the tissue volume border occupied by the locator elements can be determined under x-ray or other visualization technique with greater accuracy.

When the desired number of locator elements 200 have been deployed to define and substantially bound the tissue volume, the remaining components of system 100 may be removed and the tissue volume may be excised.

Each component of system 100 of the present invention as well as a detailed description of the various techniques for its use will now be described in detail.

FIGS. 3A–3D depict various embodiments of the locator element 200. In FIG. 3A, a particularly useful variation of element 200 is shown in perspective as having a straight and flat configuration as it assumes when disposed in the confines of a deployment tube 300 lumen.

A proximal portion 210 of locator element 200, preferably having a smaller cross-sectional area than a distal portion 220 of locator element, is shown. Proximal portion 210 transitions through a radius to distal portion 220 at shoulder 240. Preferably, the entire locator element 200 is a single-piece article having no joints or the like. When a single piece, the proximal portion 210 may be formed by laser or photoetching, traditional, electron-discharge or water-jet machining, cutting, or other techniques to reduce its cross-sectional area relative to distal portion 220. Alternatively, proximal portion 210 may be a separate article joined to distal portion 220 at shoulder 240 by any appropriate technique, such as soldering, welding, brazing, adhesives, or the like.

We prefer proximal portion 210 and distal portion 220 to each have a similarly square or rectangular cross-sectional profile, but other profiles such as circular, elliptical, and irregular are also contemplated. The cross-sectional profile of proximal section 210 need not be the same as the cross-sectional profile of distal portion 220. Furthermore, while FIG. 3A shows only a width difference between proximal portion 210 and distal portion 220, these portions may also differ in thickness as well.

The smaller cross-sectional area of proximal portion 210 compared to the distal portion 220 (as well as any possible differences in material properties when these portions are made from dissimilar materials) reduces the flexural modulus of proximal portion 210 relative to distal portion 220. This affords greater flexibility or bendability to the device so as to reduce the risk of locator element breakage, injury to others, and tissue trauma when proximal portion extends from the surface of the skin after locator element deployment but before excision. Preferably, proximal portion 210 is flexible enough to be freely and safely manipulated; for instance, proximal portion 210 can be taped or affixed to the patient's skin after deployment. This eliminates the need to have the tissue volume immediately excised, freeing the patient to leave and return for the excision at a later time.

Not only does this help to decouple the radiologist from the surgeon, but it gives the patient more flexibility to do as she pleases and certainly less invasive discomfort.

Shoulder 240 at the transition of the proximal and distal portions of locator element 200 is a particularly useful optional feature. Shoulder 240 provides an engaging or abutting surface against which the radiologist or surgeon may advance the distal end of the pusher assembly 700 (see FIG. 3B) so to move locator element 200 out the distal end of deployment tube 300 and into the tissue. Furthermore, it provides a stop against the tissue to prevent locator element 200 from backing out accidentally.

Distal portion 220 of locator element 200 is shown in FIGS. 3A and 3B as having a rectangular cross section and a distal end 230 that forms a blade or cutting surface. Alternatively or in addition, one or both of leading edge 250 or trailing edge 260 may form a blade or cutting surface. The particular shape of the distal end 230 and the cutting surface or surfaces are determined by the particular tissue in which the locator element 200 is designed to be placed and other clinical and practical parameters. The configuration of FIG. 3A is but one of many possible to provide the most efficient advancing surface for moving through tissue.

FIG. 3C shows an alternative configuration in which locating element 200 is connected to source of energy 265, preferably radio frequency (RF) energy, through lead 270. In this embodiment, RF source 265 may be a BOVIE (Leibel-Flarshiem Co., Cincinnati, Ohio) unit or the like to deliver high frequency current to locating element 200. When so energized, the distal portion 220 of the locating element becomes an active electrode which can cut through and optionally cauterize tissue as is well-known to those of skill in the art. RF may be used alone to cut through tissue or may be used in conjunction with mechanical cutting means to assist in advancing the distal portion 220 of locating element 200 through tissue.

Energy source 265 may provide other electrical energy forms to locator element 200, or it may also or instead be a source of mechanical, thermal, acoustic or other type of energy as may be desired.

When providing RF energy, source 265 not only can aid in advancing the distal portion 220 into position around the tissue volume by cutting through the tissue, it can also be used to aid the surgeon in excising the tissue volume from the body of the patient, for instance, when the energized locator element 200 (or array of elements) is rotated through an angular displacement as will be discussed in greater detail.

In order to facilitate this rotational cutting action, distal portion 220 of locator element may incorporate a leading edge 250, a trailing edge 260, or both, as shown in FIG. 3C. These portions 250 and 260 preferably but not necessarily will have a sharpened profile so to provide a cutting surface for displacing tissue and providing a focus for the high frequency energy.

One particularly usefull variation of this configuration is shown the FIG. 3D cross-section of a distal portion 220 of locator element 200 that may be used with RF energy. Here, an insulative coating or layer 280 covers the two opposing surfaces of the locator element 220 adjacent leading edge 250 and trailing edge 260. Such insulation 280 serves to electrically isolate the surfaces covered by the insulation and further focuses the RF energy on the leading and trailing edges. Insulation 280 may comprise a ceramic or metallic oxide (such as alumina, tantalum oxide, titanium oxide, etc.), a biocompatible polymer or any other suitable biocompatible electrically insulating material. Insulation 280 may be in the form of a coating that can be applied by well-known deposition methods such as physical vapor deposition (including sputtering, evaporation, ion plating, ion beam-assisted deposition, ion implantation, etc.), diffusion (e.g., cementation), electrophoresis, anodizing, plating, chemical vapor deposition, pulsed laser deposition, painting, dipping, electroplating, laser surface processing, thermal spraying, etc. Insulation 280 may also be formed in situ via surface oxidation, etc. Insulation 280 may completely cover the opposing surfaces of distal portion 220 as shown in FIG. 3D; alternatively, insulation 280 may cover only portions of these surfaces or additionally cover portions of leading edge 250 and trailing edge 260. The amount of surface area covered by insulation 280, as well as the insulation thickness, compositional profile, density, and other properties may be tailored for the particular tissue and application in which the locating element 200 is designed to operate.

We prefer that insulative coating 280 has a low coefficient of friction to ease the movement of locator element through tissue. It is even contemplated that the locator element be coated with a noninsulative but low-friction coating, whether the device is used with RF or other energy or not, simply to achieve this goal.

FIG. 3E shows another variation of locating element 200 in which a flexible wire, cable, suture or the like 290 is attached to locating element via eyelet 292. As can be seen, the overall length of locating element 200 can be considerably shorter than other variations, as the cable 290 may be viewed as taking the place of locator element proximal section 210. A suture 290 is even more suitable than the proximal portion shown in FIG. 3A for presenting a flexible, safe, and effective "lead" that may extend out through the breast surface after the locator element has been placed in the tissue.

Threading wire 290 through eyelet 292 is but one of a wide variety of ways to connect wire 290 to locator element 200. More than one eyelet may be present, for example, if it is desire to attach multiple sutures or other elements to locating element 200; alternatively, multiple sutures or other elements may be attached to locating element via a single eyelet 292. In addition, eyelet 292 or an equivalent attachment junction may be disposed distally of proximal end of locating element 200, either centrally or on one side thereof.

Locator element 200 is designed to assume a generally arcuate or curvilinear shape when unconstrained or when deployed in tissue. As such, we prefer that locator element 200 comprise a material having a shape memory, such as spring steel, stainless steel, nickel-titanium alloy such as nitinol, a shape memory polymer, or other such materials. It is preferred that locator element 200 be nickel-titanium, although less desirable alloys (from a toxicity standpoint) that exhibit shape memory characteristics, such as copper-zinc-aluminum, copper-aluminum-nickel, copper-zinc-silicon, copper-zinc-lead, gold-cadmium, and nickel-cadmium, are contemplated as well. Both superelastic stress-induced martensitic materials (i.e. temperature-independent) as well as temperature-dependent one- and two-way shape memory materials are contemplated for locator element 200. Such materials and their behavior are described in U.S. Pat. Nos. 3,174,851, 3,351,463, 3,753,700, 4,665,906, 5,067, 957, and 5,190,546; the entirety of each is hereby incorporated by reference.

The particular degree of curvature and shape of locator element 200 when unconstrained or constrained only by tissue may be designed into the element for a variety of tailored applications as is well-known in the art. It is within the scope of this invention, for instance, to supply a kit to the radiologist having a variety of locator elements with differing loop diameters and perhaps differing shapes from which to choose. A template or similar instrument that may be held up to an x-ray of the tissue containing the lesion 20 and surrounding tissue volume 22 may be provided as well. This would allow the radiologist to accurately select the proper locator element for deployment into the particular tissue of interest.

Locator element may be mechanically straightened to assume a first generally linear or flat configuration as it is inserted into deployment or delivery tube 300 or equivalent constraining member. As the distal end of the locator element 200 is deployed beyond the distal end of delivery tube 300 into the tissue of interest by pusher assembly 700, locator element 200 naturally assumes a second, substantially arcuate or curvilinear profile discussed above as it penetrates tissue and defines a tissue border along a path. The tissue border defines a tissue volume containing the targeted lesion that is to be excised. Preferably, locator element 200 does not penetrate the tissue volume as it is deployed. This shape transformation described above is preferably entirely temperature-independent; that is, it may take place at a single temperature simply upon removing the physical or mechanical constraint of tube 300 or the like as it deploys into tissue or a cavity. However, it is contemplated that materials exhibiting temperature-dependent transformation properties; for instance, those materials which can be engineered to transform from a flat, planar shape into an arcuate or curvilinear shape upon reaching a temperature threshold (such as body temperature), may be used for locator element as well.

The particular arcuate or curvilinear shape discussed above may widely vary depending upon a variety of factors; e.g., the type of tissue the locator element 200 is designed to mark, the size and location of the tissue volume, the deployment configuration (i.e., polar, tangential, etc. as will be discussed later), and other factors. Locator element may also assume more complex shapes having more than a single curve or even curves that change direction.

We also prefer that locator element 200 be at least partially radiopaque so that it may be readily viewed under x-ray energy. This aids the radiologist in placing locator element 200 in the desired tissue position as well as allowing for verification of its location and orientation. Locator element may be radiopaque by virtue of its inherent material properties; i.e., nitinol exhibits both a shape memory effect and some radiopacity as well, making it a suitable material for use in the locator element. The radiopacity of locator element 200 may be enhanced by adding a variety of components comprising materials exhibiting greater radiopacity, such as bands or elements made from platinum, palladium, tungsten, gold, silver, etc., that may be bonded or otherwise affixed to locator element 200 in predetermined locations (such as, e.g., along the leading edge 250 and trailing edge 260 or on the distal end of locator element 200). If locator element distal section 200 is insulated, such insulation may be radiopaque as well. For instance, polytetrafluoroethylene doped with barium sulfate or some other appropriate radiopaque material is suitable for this purpose.

As shown in the various figures, the distal portion 220 of locator element 200 preferably comprises a ribbon having a rectangular cross section. Such a shape provides a surface against which the surgeon may cut when excising the tissue volume contained by the locator element. In addition, when the distal portion 220 is radiopaque, the orientation of the locator element can be readily determined under x-ray visualization depending upon which surface (i.e. a leading or trailing edge as opposed to a wider surface) is presented to the viewer. Even if the deployed locator element 200 occupies multiple planes in the tissue with respect to the x-ray or ultrasound source, such information should be readily visible due to the asymmetric shape of ribbon locator element 200.

Although we prefer that the shape of distal portion 220 be a ribbon as described above, it is not so limited. For instance, the distal portion 220 may have a circular, elliptical, oval, or irregular cross-sectional shape. Various rectangular cross-sectional shapes ranging from square to those having higher cross-sectional aspect ratios (i.e., a ribbon) are contemplated as well.

When in the shape of a ribbon, distal portion 220 of locator element 200 may be between about 1.0 mm and 7.0 mm wide and between about 0.2 mm and 1.0 mm thick; we prefer it to be between about 2.0 mm and 5.0 mm wide and about 0.5 mm and 0.8 mm thick. Other cross-sectional shapes preferably are on the order of the same dimensions as those recited above.

If a shoulder portion 240 is present, it may transition from the ribbon portion having a rectangular cross section to a proximal portion 210 having a generally square or rectangular cross section with a thickness preferably the same as that of distal portion 220 and a width on the order of approximately 30 percent to approximately 80 percent of the width of distal portion 220. The particular ratio of the widths of proximal portion 210 to distal portion 220 will depend on the design constraints associated with the particular application for which system 100 is chosen. The cross-sectional shape of proximal portion 210 does not have to be the same as that of distal portion 220.

Further aspects of locator element 200 and its operation in conjunction with the other components of system 100 are discussed below in greater detail.

Turning now to FIGS. 4A and 4B, oval deployment or delivery tube or delivery 300 is shown connected to orientation element or clock wheel 500.

Deployment tube 300 is the primary device through which locator element 200 is delivered to the targeted tissue volume perimeter. The particular design elements of tube are not critical to the operation of the invention; as long as it effectively aids in delivering locator element 200 to the proper location, deviations from the features described herein and shown in the figures are possible.

Delivery tube 300 preferably has a lumen 310 that has a generally oval cross-sectional shape to accommodate the rectangular cross-sectional shape of locator element 200 and to present a lower profile when penetrating tissue. This ensures proper deployment of locator element 200 in the desired position and angular orientation. However, cannula lumen 310 may assume a variety of other cross sectional shapes, including circular, rectangular, irregular, etc. In any event, we particularly prefer that cannula lumen 310 have cross-sectional dimensions sized so that the locator element 200 may freely axially or slideably move therein; in addition, free or limited rotational movement of locator element 200 therein is also contemplated.

We prefer tube 300 be a stainless steel hypotube or the like, although it may comprise a polymer, nickel-titanium, a composite material, or other metals such as platinum, tungsten, cobalt, titanium and their alloys.

A proximal section 310 of tube 300 terminates at interface 330 with an orientation element or clock wheel 500 as shown in FIGS. 4A and 4B. Interface 330 can be a simple recessed interference fit or other type of joint between the proximal end 310 of tube 300 and wheel 500. Interface 330 need not be permanent; it may be designed so that the proximal section 310 can be removably inserted into orientation element 500, locked in place, and removed so that another tube 300 (perhaps with a different cross-sectional shape) can be fit therein. Alternatively, orientation element 500 and delivery tube 300 may be integrally formed as a single unit so that interface 330 is simply a transition between the two.

In a preferred construction, orientation element 500 has a flange 510 bounded by serrations 520 to facilitate gripping and rotation as described below.

Another particularly useful and optional feature of clock wheel 500 is shown in FIG. 4C. Here, flange 510 has a straight or flat edge 530 to indicate to the radiologist the particular angular orientation of tube 300 selected. For instance, system 100 may be configured so that when the flat section 530 is aligned with stereotactic guide unit 80 (see FIGS. 7–9), the radiologist knows that the major axis of oval deployment tube 300, and in turn the major axis along the width of locator element 200, is aligned with the particular axis indicated by guide unit 80.

To further assist the radiologist in properly orienting deployment tube 300 and locator element 200, flange 510 may have an additional flat surface parallel to surface 530 on the opposite side of flange 510. In addition, wheel 500 may contain notches, raised sections, alphanumeric markings, electronic indicators (audible, visual, etc.), or combinations of these and other features to indicate the angular orientation of element 500 with respect to the tissue coordinate system. Any device that indicates to the user the spatial orientation of tube 300 and in turn locator element 200 is within the scope of this present invention. Orientation element 500 may be metallic or polymeric as dictated by design and functional considerations.

Turning now to FIGS. 5A–5C, trocar or blade 600 is shown partially slideably disposed in a lumen of driver tube 400. As previously discussed, blade 600 is designed for deployment through driver tube 400 to initially penetrate tissue and create an access pathway through which delivery tube 300 and eventually one or more locator elements 200 may be deployed.

Driver tube or cannula 400 is preferably oval in cross-section to present a low profile configuration (as shown in FIG. 2), although it may have a more round cross-section (as shown in FIGS. 5A and 5C) or a cross-section that conforms to the cross-sectional profile of blade 600, especially the blade distal region 620 as discussed below. In general, any cross-sectional shape for cannula 400 suitable for deploying blade 600, deployment tube 300, and locator element 200 is within the scope of the invention.

We particularly prefer that the lumen of driver tube 400 be sized so that the deployment tube 300 may freely axially or slideably move therein; in addition, free or limited rotational movement of delivery tube 300 therein is also contemplated.

We prefer cannula 400 be a stainless steel hypotube or the like, although it may comprise a polymer, nickel-titanium, a composite material, or other metals such as platinum, tungsten, cobalt, titanium and their alloys.

Trocar or blade 600 can take on a wide variety of shapes, cutting surface configurations, and features depending upon the particular design and functional constraints for the application chosen. FIGS. 5A–5C, however, show a particularly useful blade 600 design for making an initial incision into breast tissue to create an access passageway for deploying one or more locator elements as described herein.

Trocar 600 has a proximal region 610 terminating at proximal end 630 and a distal region 620 terminating at a distal end 640. In this particular configuration, distal region 620 contains blade edges 650 and the distal end 680 of tubular members or lumen 660 disposed along the length of trocar 600. Tubular member 660 may be considered an integral part of trocar 600. FIG. 5A shows one of two tubular members 660 that are better seen in cross-section of FIG. 5B. As one moves proximally along blade 600, this dual-lumen cross-sectional profile gradually transitions into one having a single lumen as is shown in FIG. 5C. Trocar 600 terminates, in this particular embodiment, in a hub 690 which attaches to an optional syringe 692.

Turning back to the distal end 640, two blade edges 650 are seen disposed along a single axis and joining at a single point near the distal end of blade 600. Blade edges 650 may take on a number of different configurations. They may be serrated, for example, and they may be capable of using electrical, acoustic, mechanical, or thermal energy as described herein. Although the particular tip features and configuration of blade edges 650 may vary considerably and be within the scope of the invention, we have found the configuration of FIGS. 5A–5C to be particularly useful for cutting through breast tissue.

Tubular member 600 is designed to alleviate some of the difficulties associated with penetrating tissue by providing a port or lumen 660 through which various agents may be administered to the patient, preferably but not necessarily while the blade is cutting through tissue. For instance, an anesthetic agent such as lidocaine gel or liquid or the like may be selectively administered to tissue through the distal end 680 of tubular member lumen 660 via a syringe 692 connected to the blade 600 at hub 690. In addition, a lubricant such as K-Y jelly (Johnson & Johnson, New Brunswick, N.J.) or liquid, a water-based lubricant, or the like, may be administered during the cutting process to reduce the coefficient of friction between the blade edges 650 and tissue as the trocar 600 cuts through the tissue. Other substances may be disposed through tubular member 660 as required, such as antithrombolytic agents, hormones, chemotherapeutic drugs, anti-scarring agents, etc. These and other substances may be administered manually by the radiologist during the procedure intermittently or continuously, or they may be automatically dispensed by any number of electronic, mechanical, or electromechanical means.

In addition, physical elements such as additional blades, individual hypotubes, fiber optics, sensors, and other devices may be deployed through lumen 660 as the radiologist or surgeon sees fit.

Although FIGS. 5A–5C show only two tubular members 660, the invention is not so limited. Any number of tubular members may be used with this invention, from one to six or more, depending upon the needs of the patient and the objective of the procedure in which blade 600 is being used.

Blade and tubular member may be metallic, polymeric, a composite material, or a combination of metals, polymers, and their alloys as described herein. Particularly useful is stainless steel. The various components of this variation of trocar 600 may be integrally formed as a single element, or they may be assembled via any number of a suitable joining techniques, such as welding, brazing, soldering, adhesives, or the like.

We prefer that blade edges 650 be hardened stainless steel so to provide a keener cutting surface that does not dull with use.

A valve and seal system as is well-known in the art may accompany hub 690 to facilitate selective administration of the desired agent.

Tubular member 660 is optional. However, its low profile and functional utility for both patient and doctor make it a clearly useful feature that effectively complements system 100.

Methods of Use

Polar Deployment

FIGS. 6–17 show, in detailed fashion, a method for using system 100 to mark a volume of tissue for eventual removal or excision from the breast, preferably without penetrating or otherwise violating the interior of the tissue volume. A particularly useful technique in which one or more locator elements are deployed in a "polar" fashion is described below.

Although this method is described in the context of removing a nonpalpable lesion from the breast, it may be followed for marking and excising any tissue mass or foreign object from the body.

In particular, a method is described below for defining the border of a tissue volume to be excised from a patient. This is accomplished by deploying at least one locating element into breast tissue so that it follows a continuous path around the selected tissue volume, thereby containing the target tissue region. Later excision of the so-marked tissue volume by a surgeon is also described.

The patient is typically first prepared for the marking procedure by placing the breast tissue 10 between two compression paddles 30 on a platform such as a Fisher Table.

The tissue volume 22 containing the suspect lesion 20, such as one or more microcalcifications, is next mapped under x-ray guidance and a three-dimensional coordinate system or grid is assigned to the tissue of interest. Typically the entire breast tissue 10 between plates 30 is mapped on a three-dimensional coordinate system. For purposes of this example, "x" and "y" coordinates in FIG. 6 are associated with a tissue location along axes in a horizontal plane parallel to paddles 30. Likewise, the "z" coordinate describes a tissue location in a vertical or depth plane perpendicular to each of the x and y axes.

FIG. 7 shows portions of system 100 after lesion 20 and targeted tissue volume 22 have been identified, centered below window 50, mapped in three-dimensional coordinates, and driver tube 400 (shown in cutaway cross-section) with attached stereotactic guide unit 80 is centered over window 50. Blade or trocar 600 is disposed in a lumen of driver tube 400.

Note that a longitudinal axis of cannula 400 is generally aligned with a vertical or z-axis of the mapped tissue such that the cannula lumen is centered over tissue lesion 20. This configures system 100 so that locator element or marker 200 deploys into the tissue 10 along this axis; hence the term "polar deployment".

Blade 600 is then deployed distally through the cannula 400 lumen so that it exits the cannula distal end and penetrates through tissue 10 to the targeted tissue volume 22 to be excised.

It is within the scope of the invention to perform this tissue penetration step in any number of ways. For instance, the radiologist may manually advance blade 600 into tissue 10, preferably with the assistance of x-ray, ultrasound, magnetic resonance, or other method. Such a technique may be preferable, especially under difficult or delicate conditions where caution and control are at a premium.

Alternatively, blade 600 may be advanced automatically, such as via a spring-loaded or similar biopsy driver mechanism as is well-known to those of skill in the art. In such a case, system 100 may be adapted to interface with any number of commercial biopsy driver systems through, for instance, an optional driver positioning or interface member. Pusher assembly 700 may also be used to advance blade 600 into tissue 10.

Typically, blade 600 will penetrate tissue 10 so that its distal end 640 just reaches the vicinity of the surface or border of tissue volume 22. In the case of a polar deployment scheme, blade distal end 640 will reach the border of tissue volume 22 along the z-axis as described above, while other deployment schemes may dictate deployment at other locations along or near the border of tissue volume 22.

Preferably, the blade 600 distal tip 640 does not penetrate into the tissue volume 22. If the tissue volume 22 is inadvertently or intentionally penetrated, however, care should be taken to preserve the integrity of tissue volume 22 and avoid penetrating further into lesion 20.

If blade 600 is equipped with one or more tubular members 660 as previously described, lubricating agents, anesthetics such as lidocaine, or any number of other appropriate pharmaceutical agents may be administered through the tubular member lumen 660 so that they are deployed into the tissue through tube distal end 680. Preferably such agents are administered simultaneously as the blade 600 is advanced into tissue 10; however, they may be administered before or after the pathway is created. In addition, one or more sensors, fiber optics, electrocautery electrodes (to control bleeding during cutting), or other devices may be deployed through lumen 660.

FIG. 8 shows system 100 after blade has been proximally withdrawn from tissue 10 and cannula 400 and a conventional trocar 420 has been deployed into the lumen of driver tube 400 until its distal end 430 extends distally of the distal end of cannula 400. Trocar 420 and cannula 400 may then be advanced as a unit, or with the trocar leading in sequential deployment, into the tissue 10 through the pathway created by blade 600 to further define and enlarge it. Preferably, however, and as shown in FIG. 8, trocar 420 is advanced just to the edge or border of tissue volume 22 as previously described for deployment of blade 600 while the cannula 400 does not extend into tissue 10.

Trocar 420 is then removed by proximally withdrawing it from driver tube 400, leaving tube 400 in place either at the skin surface at the entry point of trocar 420 (as shown in FIG. 8), slightly into the aforementioned pathway, or deep enough into the pathway such that cannula 400 now occupies and even may be considered part of the pathway itself.

It should be noted that the steps heretofore explained in which a blade, trocar, and cannula are used to create the access port or pathway in tissue 10 to reach tissue volume 22 may be performed in any sequence or in any of a number of ways not described herein but are as known to those of skill in the art. It is not critical to the invention for the pathway or port to be created as described above. The steps described above are merely exemplary of a method we have found to be useful; as long as a port is created in which the invention as described herein may be practiced, any method is acceptable.

FIG. 9 shows cannula 400 after trocar 420 has been withdrawn and oval deployment tube 300 is inserted through the driver tube 400 lumen and advanced distally to the vicinity of the border of tissue volume 22. Preferably, but not necessarily, tube 300 is advanced to a position just proximal to tissue volume 22 at the distal end of the tissue pathway as shown in FIG. 9.

Deployment tube 300 is shown in FIG. 9 connected to an orientation element 500 for indicating the alignment of locator element 200 as described above.

FIG. 10 depicts the next step. Distal portion 220 of locating element 200 has a ribbon or similar cross-sectional profile in which its width is larger than its thickness. The proximal portion 210 of locator element 200 is disposed in pusher tube 730, which in turn are disposed in deployment tube 300. This assembly is then placed in the lumen of cannula 400.

The FIG. 10 view of locator element is looking along its width, so that only the uniform thickness of the locator element 200 as one moves from proximal portion 210 to distal portion 220 can be seen. Therefore, only the edge of shoulder 240 is seen. However, the distal end of pusher tube 730 is shown abutting shoulder 240 so that as the proximal portion 210 of locator element 200 is distally advanced into the tissue, the distal portion 220 of locator element 200 exits the distal end of deployment tube 300 to enter the tissue 10 in the vicinity of tissue volume 22.

For purposes of this illustration, oval tube 300 preferably is manipulated via orientation element 500 so that the major axis of the oval tube 300 cross section and the aligned width of the accompanying locator element are parallel to the y-axis. This helps to ensure that the deployed locator element 200 maintains the desired orientation with respect to the tissue 10 and the coordinate system, giving the radiologist important information relative to the location and orientation of the tissue volume 22 when marked. The surgeon will benefit from such an orientation as well when cutting around the surface of the ribbon along its width to more readily excise the tissue volume 22.

Once the deployment tube 300 and, simultaneously or subsequently, the locator element 200 is advanced so that their distal ends are in position in tissue 10, the locator element 200 is further advanced distally out of tube 300 distal end as shown in FIG. 10. As element 200 exits tube 300, it preferably will take on its predetermined shape and penetrate the tissue 10 to begin to define a tissue volume border 24 along a path. This border 24 in turn partially defines the tissue volume 22 to be excised by the surgeon.

Note that this illustrates a "polar" locator element deployment scheme. That is to say, proximal portion 210 of locator element 200 has a longitudinal axis that is substantially aligned or overlapping with the z-axis or central axis of the tissue volume 22. See the single dashed line bisecting lesion 20 in FIG. 10, which represents the position these axes take.

This ensures that the distal portion 220 of locator element 200 enters the tissue 10 at an initial point that is aligned with the central tissue axis or z-axis of tissue volume 22 and lesion 20.

FIGS. 11–13 show successive views of locator element 200 as it continues to advance along a path to define a tissue border of tissue volume 22 (now with stereotactic guide unit 80 removed for clarity). As the radiologist causes the pusher assembly 700 to advance distally, the distal end of pusher tube 730 continues to engage shoulder portion 240 to likewise distally advance the locator element 200.

As it deploys, the element 200 (and the path it occupies) preferably takes on an arcuate or curvilinear shape. More preferably, element 200 takes on a loop shape having a diameter greater than about 8 mm; more preferably greater than about 9 mm;

even more preferably greater than about 1 cm. Locator element 200 may also take on a number of other shapes once deployed as previously discussed. The particular shape of the locator element is dictated by the shape of the tissue volume 22 and the particular tissue being excised.

A particularly useful feature of system 100 is that locator element 200 deploys along the first path in the tissue volume border 24 such that the distalmost portion of the tissue volume is encompassed by the path formed by the locator element 200.

Said another way, we prefer that the distal portion 220 of element 200 extend to or even around the distalmost portion of tissue volume 22 (as measured in a downward direction along the z-axis) such that the element 200 bounds the tissue volume 22 containing the targeted lesion 20 along a continuous path. This path may be viewed as forming a physical border around the majority of the perimeter of the tissue volume 22. In the examples of FIGS. 10–13, distal portion 220 of locating element 200 continues well past the most distal portion of tissue volume 22 and forms a loop that substantially encompasses the border 24 along this path.

There are at least two significant advantages to this feature of system 100. First, when the locator element 200 is deployed into position as described above, manipulation of a proximal portion 210 of the locator element 200 will result in an equivalent or proportional manipulation of the tissue volume 22 enclosed by the element 200. For instance, if a proximal portion of element 200 is moved along the z axis, the targeted lesion 20 and enclosing tissue volume 22 will move an equal or proportional distance along the z axis. Likewise, pivoting or otherwise manipulating proximal portion 210 will result in a concomitant pivoting or other movement of the enclosed tissue volume 22. If the proximal portion 210 is replaced by a flexible cable, wire or suture as discussed above, manipulation of the wire results in a likewise and proportional manipulation of tissue volume 22.

A second important advantage of this feature of system 100 is that the surgeon may excise the tissue mass 22 by cutting along the surface of the locator element opposite the tissue volume and be confident that the entire volume 22 will be excised because the distalmost portion of the volume is encompassed by the locator element 200.

If, either during deployment or after full deployment of locator element 200 in the tissue 10 as described above, the radiologist may wish to partially or completely remove the element 200 from the body. For instance, if the locator element 200 is misdeployed or if there is a malfunction of some component of system 100, it may be desirable to reposition or even completely remove locator element 200 from the body.

The radiologist simply pulls the proximal portion 210 or wire 290 in the proximal direction so that the locator element 200 retreats proximally into deployment tube 300, and straightens into its predeployment shape. She may exert opposite force in the distal direction on the pusher assembly 700 to provide leverage. Of course, the thumbscrew 720 in ferrule 710 should be loose to allow relative movement between the locator element 200 and pusher assembly 700. When the shoulder 240 retreats to an abutting position against the distal end of pusher tube 730, the radiologist may tighten thumbscrew 720 to fix the locator element proximal portion 210 in the ferrule 710 and continue to pull either the locator element or the affixed pusher tube proximally to further withdraw the locator element as she sees fit.

The unique profile and shape of the various locator element embodiments discussed and shown herein at least partially account for this feature of the invention. For instance, there are no barbs or hooks on locator element which would otherwise hinder or make reverse movement of the locator element 200 impossible. Furthermore, when element 200 is comprised of spring steel or a shape memory alloy such as nitinol, the element 200 may be straightened as it is proximally retracted into deployment tube 300 without little to no plastic deformation. This also serves to facilitate locator element 200 retraction and redeployment.

At this point, if the radiologist is satisfied with the position of locator element 200 in the tissue 10, she may decide to refrain from deploying one or more additional locator elements and present the patient to the surgeon for removal of the tissue volume 22. This is perfectly acceptable and is within the scope of the invention. For instance, the lesion may be well-defined and conditions are such that excision of tissue volume 22 along a single locator element may be confidently accomplished.

However, to further define the tissue volume 22 along a different plane, at least one additional locator element may be deployed in the tissue. This is shown in simplified FIGS. 14–16 and discussed below.

As seen in FIG. 14, the radiologist will preferably first rotate or otherwise manipulate orientation element 500 through a selected angular displacement so that the major axis of the deployment tube 300 in turn is rotated an identical or proportional amount as desired. In this example, orientation element 500 is rotated ninety degrees so that the major axis of tube 300 and, when inserted into tube 300 lumen, the accompanying width of locator element 200' is oriented ninety degrees with respect to the width of deployed locator element 200, or so that the locator element 200' will deploy in a second path that is generally parallel to the y-axis.

Either before or after such rotation, second locator element 200' is inserted and advanced distally into the lumen of deployment tube 300 as previously described with respect to the first locator element. Preferably, under x-ray or other visualization technique guidance, the second locator element is advanced through the distal end of the tube 300 and penetrates tissue 10 so that locator element 200' further defines the tissue border 24 along a second path without penetrating tissue volume 22.

As the second element 200' is advanced along the second path, a second plane is defined that is preferably non-parallel to the plane defined by the first locator element 200. In this example, the second plane is angularly displaced approximately ninety degrees with respect to the first plane in accordance with the amount of rotation deployment tube 300. This is shown along a "polar" z-axis in the view of FIG. 15, looking down at the tissue volume 22 in the z direction, where the angular displacement a between the first and second locator elements 200 and 200' can be readily seen.

When two locator elements are used to mark the tissue volume 22 for excision, we prefer to deploy the second locator element 200' so that it is angularly displaced in the tissue approximately ninety degrees with respect to the first locator element 200 as discussed above. Such a displacement is preferred, especially when each element is radiopaque and similarly shaped (i.e., a ribbon or other asymmetric cross-section), because of the ease with which the radiologist can view an x-ray image of the deployed locator elements and determine their orientation with respect to the grid assigned to the tissue. This is especially true when the first locator element is deployed into a path parallel to the x-axis, as a ninety degree angular displacement of the second locator element about a polar axis will by definition place its path parallel to the y-axis.

Alternatively, the first and second locator element 200' may be angularly displaced approximately forty-five degrees with respect to one another. This may be preferred, for instance, if a third locator element is used, or if the particular lesion 20, patient condition, practitioner preference, or combination of these or other factors so dictate.

It is within the scope of the invention, however, that the second locator element 200' be displaced at any angle with respect to the first locator element around the common polar or z-axis. This is why the orientation element 500 may be infinitely rotatably variable; alternatively or additionally, it may rotatable in fixed angular increments.

At this juncture, tissue volume 22 containing the suspect lesion 20 is bounded by first locator element 200 and second locator element 200' as schematically shown in FIGS. 15 and 16. Tissue volume 22 may be removed by any number of techniques as discussed below. However, a third locator element 200" (not shown) may also be deployed as previously described so that at least a portion of the third locator element 200" further defines the tissue border along a third path. This third path will preferably define a third plane that is non-parallel to the first and second planes.

For instance, third locator element 200" may define a third plane when deployed which is angularly displaced approximately forty-five degrees from each of the first and second planes. It is within the scope of the invention, however, for each of the locator elements 200, 200', and 200" to be disposed at any angle with respect to each other. Furthermore, the angles between any two of the elements may be different.

Additional locator elements may be used to further define the tissue volume 22 prior to excision as required.

Once the desired number of locator elements have been deployed into the tissue to define the tissue volume 22, the tissue is decompressed and removed from paddles 30, and the remaining components of system 100 may be removed from the site so that only the locator element and any proximally attached elements (such as flexible wire or suture 290) remain in the tissue 10. This is shown in FIG. 17 for the two-element deployment described above. Note that a proximal portion 210 of each locator element (or alternatively flexible wire or suture 290) extends through the skin surface. When the entire locator element is inside tissue 10 and a suture is attached at the locator element proximal end, the suture should extend through the tissue 10 and the skin surface so that it may be manipulated.

One advantage of this portion of the tissue marking and removal process is that if the other components of system 100 are removed from the vicinity of tissue 10, leaving only one or more locator elements and perhaps an attached suture extending through the skin surface, the tissue volume 22 does not have to immediately be excised as is the case with other tissue marking devices. The proximal portion 210 of locator element or the suture 290 is flexible enough that it may be taped or otherwise affixed to the patient's skin so that the patient may wait up to several days or more, with the chance to go home, before the volume 22 is removed by the surgeon. In this manner, the patient can be scheduled for excision at a convenient time within minutes or up to several days from the time of deployment.

Once the patient and surgeon are ready to excise the tissue volume 22, the patient is put under anesthesia and the surgeon accesses the tissue volume using conventional surgical tools such as scalpel 90. She will cut around the outside surface of the locator elements to separate the tissue volume 22 from tissue 10 and then remove the tissue volume from the body. This is illustrated in FIG. 17.

In general, the surgeon will first reach the tissue volume through any number of approaches. Some situations will dictate that the surgeon access the tissue volume 22 by cutting into the tissue 10 along the proximal portion 210 of the one or more locator elements 200 or along the flexible wire or suture 290 attached to the locator element. Such an approach may be favored if the tissue volume 22 is near the surface of the skin and cutting along this path is the shortest and most clinically acceptable path. If the locator element deployment tube 300 is still in the tissue 10, the surgeon may readily access the locator element along its surface, which is easy to locate and follow with a scalpel to the locator element.

Alternatively, the surgeon may wish to approach the locator element along a path different than the proximal portion of locator element or suture. Under x-ray or other type of guidance, for instance, the surgeon may penetrate through the tissue 10 at a second site such as that shown in FIG. 17 as path 92 if, for clinical, cosmetic, or other reasons it is preferable to do so. When the locating element is disposed in breast tissue, a circumareolar approach 94, which minimizes the appearance of any scar, may be preferred. It should be noted that when an alternative surgical path to reach and remove the locator element and the enclosed tissue, even the proximal portion of locator element may be removed through this alternative path as formed by the surgeon. This allows the relatively small incision diameter through which the locator element was originally deployed to remain basically undisturbed.

In any event, the fact that the surgeon may access the tissue volume 22 along a path different than the initial deployment path for system 100 is because the tissue volume 22 is now "palpable" in the sense that its border or perimeter is defined and occupied by one or more locator elements that can be palpated. The tissue volume 22 is in a sense encapsulated by the locator elements.

Once the surgeon has cut through tissue 10 to reach the locator elements, she will next begin cutting through tissue 10 substantially along a surface of the locator element 200 which is opposite a surface of each locator element 200 disposed immediately adjacent the tissue volume 22. In other words, the surgeon will find the outside of the "cage" formed by the one or more locator elements and begin cutting along its surface to separate tissue immediately adjacent the outer surface of the "cage" from the tissue enclosed but not penetrated by the one or more locator elements.

As the surgeon cuts along the outer surface of the locator elements, she is able to discern the volume by visual and tactile cues, aided by her experience, and will cut around tissue volume 22 without penetrating it. Eventually, she will cut tissue volume 22 free from the surrounding tissue 10 so that it may be lifted with the locator elements enclosing the volume out of the tissue 10.

Methods of Use
Tangential Deployment

There may be instances when it is desired to deploy one or more locator elements into the tissue 10 from an access point other than the polar location described above.

FIGS. 18–19 show a deployment of one or more locator elements 200 via an alternative tangential deployment technique. Here, the initial point of deployment of the distal end of the locator element 200 as it extends out of the deployment tube 300 lumen is substantially along a line that is tangent to the tissue volume 22 to be removed.

In contrast to the polar configuration of FIG. 13, a longitudinal axis 95 of a proximal portion of the locator element 200 is now substantially aligned with a tangential axis 96 of tissue volume 22 instead of a tissue volume central or polar (z) axis 98. This is shown for a single locator element in FIGS. 18A (perspective view) and 18B (planar view looking along the z-direction).

Note that if more than one locator element is deployed tangentially, the initial point of entry into the region of the tissue volume 10 border or perimeter will be along a different tangential tissue volume axis for each locating element. This may require multiple access ports be created in the tissue 10 via the blade 600 and driver tube or cannula 400, each aligned with the tangential axis along which a path or border will be created as the respective locator element is deployed along the perimeter of tissue volume 22. FIGS. 19A and 19B depict two locator elements 200 and 200' defining the border or perimeter of tissue volume 22 after having been tangentially deployed along tangential axes 102 and 104, respectively, as described above.

This is in contrast to the polar technique described earlier, in which each locator element generally deploys into tissue along a single central or polar axis of the tissue volume, thus requiring only a single tissue passageway as previously described.

Methods of Use
Additional Energy Source

FIG. 20 depicts an alternative method in which a source 265 of energy is connected to locator element via a transmission cable 270, handle 272, and clamp 276. As previously described, there may be instances when it is preferable to energize the locator element or elements with RF energy to cut through tissue as an alternative means for removing the tissue volume 22 from the body once it is defined by the locator element or elements. For instance, one edge along the thickness of locator element 200 may be conductive and exposed (i.e., noninsulated) such that when energized by a source of RF energy, the locator element may be rotated as a single unit or "cage" through an angular displacement to cut through the tissue border defining tissue volume 22, removing it from the rest of tissue 10. The particular degree of angular displacement required to cut through the tissue volume 10 border so that it may be excised will of course depend on the number of locator elements present and their relative angular displacement.

Clamp 276 should be electrically conductive so to transmit the RF energy to the locator elements. A transmission cable 270 connected to either the clamp, the handle 272, or both, provides a conduit for delivering RF energy to the locator elements. An optional ground plate or similar return electrode (not shown) may be disposed on the patient's skin on tissue mass 10 or any other suitable part of the patient's body. Alternatively, the system may be configured to operate in bipolar mode with no need for a return electrode.

Energy source 265 may also be used to energize the locator element to provide electrocauterizing energy to the tissue as it is being excised so to minimize bleeding, etc.

RF energy source may also contain or alternatively be a thermal energy source, such as a laser or the like, for delivering thermal energy to the locator element and tissue volume 22. Transmission cable 270 in this instance may comprise a fiber optic cable, for instance, to transmit this thermal energy. It is also within the scope of the invention to additionally or alternatively include a source of mechanical or acoustic (such as ultrasonic or vibrational) energy for supplementing or substituting for the other types of energy discussed herein.

One particularly useful configuration is where at least one edge 250 or 260 of the locator element forms a cutting surface or blade to cut through tissue when the locator element is rotated as described above. This type of locator element may also be complemented by RF or other energy sources to assist the locator element cutting surface in cutting or separating tissue 10.

This invention also contemplates the use of techniques to monitor and control the output from a high frequency power supply or other energy source such as RF unit 265. For instance, a neutral electrode can be used in conjunction with the locator element (which may act as an active electrode) to detect current leak, to detect impedance of the circuit and the tissue, or sense the temperature of the tissue in the vicinity of the active electrode (locator element). Both monopolar and bipolar configurations are possible. Measurement of these and other feedback data may be used to manually or automatically control the RF source 265 output level, for instance. Such systems are widely known in the art as described in, for instance, U.S. Pat. Nos. 5,540,683 to Ichikawa et al., U.S. Pat. No. 5,300,068 to Rosar et al., and U.S. Pat. No. 6,019,757 to Scheldrup, each of which is hereby incorporated by reference.

Although the foregoing discussion is in the context of the marking and removal of a nonpalpable mass or lesion located within a human breast, the invention is not so limited. This invention may be used to fixedly and removably place one or more locator elements in tissue in a wide range of sites in the body.

For instance, system 100 may be used to mark tissue in any number of organs (e.g., breast, liver, lungs), muscle or fat tissue, or even cavities such as the abdominal cavity. It is also within the scope of the invention that foreign objects such as bullets, etc. may be marked for removal by system 100. The versatility of system 100 for use in such a wide variety of applications is highlighted by the number of configurations, shapes, and system 100 may take and the variety of methods in which system 100 may be deployed.

In-Situ Formation of Locator Element

Turning now to FIGS. 21–23, an alternative locator element 205 is shown being formed in situ by an alternative deployment tube 305.

This alternative embodiment is best described in the context of the method of using system 100. Although deployment tube 305 and locator element 205 are slightly different than their counterparts described above, this embodiment is deployed largely as previously described with the exceptions noted below.

Alternative locator element 205 is shown in a flat and straightened form in FIG. 21A. Element 205 is largely identical to locator element 200 previously described except that it is capable of being plastically deformed upon advancing through the deployment tube 305 and die 307 as discussed below. This feature may be described as a cold-die forming technique similar to draw or compression processes as are well-known in the materials processing industry.

FIG. 21A shows a locator element 205 formed into a flat shape prior to deployment in the tissue. Locator element should have any desired features, such as the profile of the distal end, any cutting surface, and any proximal hole for attachment of a suture, etc., incorporated into the element prior to deployment in tissue 10. Care should be taken to ensure that any coating on locator element 205 will not be marred or abraded by the process described below.

In FIG. 21B, locator element 205 is shown being distally fed into a lumen 303 of deployment tube 305 via a pusher 700 (not shown). The cutaway profile of the distal region of tube 305 reveals the path element 205 takes as it travels distally through tube lumen 303 and approaches cold-forming die 307 and die cavity 309. Die and die cavity are configured to bend the distal portion 207 of locator element 205 as it passes axially through die cavity 309 and into the tissue 10 to define a tissue border along a path that in turn defines tissue volume 22. FIG. 21C schematically depicts this process with tissue volume 22 removed for clarity.

Once locator element has been plastically deformed in this manner and has passed completely through die cavity 309 to take on the loop or arcuate configuration shown in FIG. 21D, the deployment tube 305 containing die 307 is proximally withdrawn or rotated for the optional deployment of an additional locator element as discussed in detail above.

Preferably, locator element 205 is a ribbon or similar form having a width larger than its thickness. Of course, die 307 and die cavity 309 are appropriately shaped to impart the proper amount of plastic deformation for the dimensions of locator element 205 and the material used so to exceed the elastic limit of the locator element while avoiding overstressing it, which could cause edge or surface cracking that could interfere with the element's performance. More or less severe curves than that shown for die cavity 309 are within the scope of the invention. Other die cavity profiles may include irregular and other various shapes, such as reverse curves, etc., so that a variety of desired final shapes of the formed locator element 205 may be realized.

Care should be taken to ensure that the surfaces of die that form the die cavity 309 are smooth so to avoid creating surface irregularities in the locator element or damage to the insulating or other material that may be coated onto the element 205 surface as described above.

Die 307 may be made of any appropriate material suitable for serving its intended purpose. Preferably the die comprises a biocompatible tool steel such as a tungsten or low-alloy steel or other metal, alloy of such, or composite as may be appropriate. Locator element 205 may comprise any suitable material as discussed above, including those materials that do not exhibit shape memory characteristics. Other than the typical materials requirements such as biocompatibility, radiopacity, etc., the material should at least also be selected to allow the locator element to exceed the elastic limit so to plastically deform into the permanent shape as it is passed through die 307.

FIG. 22 depicts an embodiment of the invention in which a die 311 having a positive curve 313 and a reverse curve 315 is used to cold-form a locator element while simultaneously deploying it in a polar configuration. Here, die cavity 317 first subjects the flat locator element to a reverse curve 315 as it is advanced by pusher 700. This deforms element 205 into a first curve which prepares and aligns it for the proper final shape as it is formed through positive curve 313 and exits die cavity 317 in the desired arcuate or loop shape. Such a die allows locator element 205 to deploy in the preferred polar configuration as discussed above. As with the previous examples, curves 313 and 315 may have a variety of curvature radii, differing radii; the die may also have additional curves if so desired.

FIG. 23 depicts a variation of the embodiment of FIG. 22 in which die 317 is adjustable. As shown, lead screw 319 or a similar element is rotatably disposed in a lumen of the upper portion 321 of the die that is slideably affixed to die lower portion 323. Rotation of screw 319 in either direction moves upper portion 321 distally or proximally relative to lower portion.

The distal end 325 of lower portion of the die is curved so to impart a particular curvature to die cavity 327, thereby imparting a corresponding curvature to locator element 205 as it passes through. Distal end 329 of die upper portion is appropriately shaped with a positive curve to impart a final shape to locator element 205 as discussed with respect to the FIG. 22 embodiment. However, the axial adjustability of the upper portion 321 allows the distal ends of each portion of die 317 to form a variety of positive curve shapes that in turn will form locator element 205 rings having a variety of different diameters, ranging preferably from between about 0.5 cm to about 3.0 cm or more.

Lead screw 319 is but one of any number of mechanisms suitable for adjusting the axial position of die upper portion 321 relative to die lower portion 323 within the scope of the invention.

The invention herein has been described by examples and a particularly desired way of practicing the invention has been described. However, the invention as claimed herein is not limited to that specific description in any manner. Equivalence to the description as hereinafter claimed is considered to be within the scope of protection of this patent:

We claim the following:

1. A tissue localizing device comprising:
   at least one locator element having proximal and distal portions, the locator element adapted to penetrate tissue so that the distal portion of the locator element defines a tissue border along a first path, the tissue border defining a volume of tissue containing a target region that is substantially bounded by the distal portion of the locator element, and the proximal portion of the locator element extends away from the bound tissue volume.

2. The tissue localizing device of claim 1 wherein the distal portion of the locator element is adapted to form a loop when deployed in tissue.

3. The tissue localizing device of claim 1 additionally comprising a second locator element adapted to penetrate tissue so that the distal portion of the second locator element further defines the tissue border along a second path, the target region substantially bounded but not penetrated by the second locator element.

4. The tissue localizing device of claim 1 additionally comprising a deployment tube having a lumen in which the locator element is slideably disposed and a distal end through which the locator element is adapted to exit.

5. The tissue localizing device of claim 4 additionally comprising a second locator element adapted to be slideably disposed in the deployment tube.

6. The tissue localizing device of claim 5 wherein the second locator element is adapted to deploy into the tissue such that the second locator element defines a second plane that is non-parallel to a first plane defined by the first locator element.

7. The tissue localizing device of claim 6 wherein the second plane is angularly displaced approximately ninety degrees with respect to the first plane.

8. The tissue localizing device of claim 6 wherein the second plane is angularly displaced approximately forty-five degrees with respect to the first plane.

9. The tissue localizing device of claim 1 wherein the locator element is at least partially radiopaque.

10. The tissue localizing device of claim 2 wherein a longitudinal axis of the proximal portion of the locator element is adapted to be substantially aligned with a radial axis of the loop formed by the distal portion of the locator element when the locator element is deployed in the tissue volume.

11. The tissue localizing device of claim 2 wherein a longitudinal axis of the proximal portion of the locator element is adapted to be substantially aligned with a tangential axis of the loop formed by the distal portion of the locator element when the locator element is deployed in the tissue volume.

12. The tissue localizing device of claim 1 wherein the locator element comprises a ribbon.

13. The tissue localizing device of claim 1 wherein a width of the locator element is larger than a thickness of the locator element.

14. The tissue localizing device of claim 1 wherein the locator element comprises a wire.

15. The tissue localizing device of claim 14 wherein the wire has a non-circular cross section.

16. The tissue localizing device of claim 1 additionally comprising a suture attached to a proximal end of the locator element.

17. The tissue localizing device of claim 1 wherein the locator element comprises a material selected from the group of stainless steel, spring steel, nickel-titanium, or biocompatible polymer.

18. The tissue localizing device of claim 1 wherein the locator element at least partially comprises a shape memory material.

19. The tissue localizing device of claim 1 wherein the distal portion of the locator element is plastically deformed while defining the tissue border.

20. The tissue localizing device of claim 1 wherein the locator element additionally comprises a shoulder portion disposed proximally of the locator element distal portion.

21. The tissue localizing device of claim 20 wherein the locator element proximal portion is disposed proximally of the shoulder, the proximal portion having a smaller cross-sectional area than a cross-sectional area of the locator element distal portion.

22. The tissue localizing device of claim 1 wherein the locator element has a cutting surface.

23. A device for defining the border of a volume of tissue having a proximal portion and a distal portion, the device comprising:
   at least one locator element having proximal and distal portions, the distal portion of the locator element adapted to penetrate tissue proximal to the tissue volume and follow a path to include the distalmost portion of the tissue volume, thereby defining a bound tissue volume, with the proximal portion of the locator element extending away from the bound tissue volume.

24. The device of claim 23 wherein the locator element comprises a ribbon.

25. The device of claim 23 wherein a width of the locator element is larger than a thickness of the locator element.

26. The device of claim 23 wherein the locator element is further adapted such that when the proximal portion of the locator element is manipulated, a target region contained within the tissue volume that is substantially bounded by the distal portion of the locator element is correspondingly manipulated.

27. The device of claim 23 wherein the distal portion of the locator element is adapted to form a loop in the tissue.

28. A tissue localization system comprising:
   a locator element deployment tube and
   at least one locator element having proximal and distal portions,
   said locator element being positionable within and deployable from the locator element deployment tube and, upon deployment, adapted to penetrate tissue so that the distal portion of the locator element defines a tissue border along a first path, the tissue border defining a volume of tissue containing a target region that is substantially bounded by the distal portion of the locator element.

29. The system of claim 28 additionally comprising an orientation element attached to the locator element deployment tube.

30. The system of claim 29 wherein the orientation element is rotatable with respect to a tissue coordinate system.

31. The system of claim 30 wherein the orientation element is rotatable in fixed angular increments.

32. The system of claim 28 additionally comprising a source of energy connected to the locator element.

33. The system of claim 32 wherein the energy source is electrical.

34. The system of claim 33 wherein the energy is radio frequency energy.

35. The system of claim 32 wherein the source of energy is thermal.

36. The system of claim 32 wherein the source of energy is acoustic.

37. The system of claim 32 wherein the source of energy is mechanical.

38. The system of claim 32 wherein the locator element is partially electrically insulated.

39. The system of claim 38 wherein the locator element has a rectangular cross section having four sides and wherein at least two of the four sides are electrically insulated.

40. The system of claim 38 wherein an electrically insulative material is disposed on at least a portion of a surface of the locator element.

41. The system of claim 38 wherein the electrically insulative material has a low coefficient of friction.

42. The system of claim 28 wherein the cutting element additionally comprises at least one lumen disposed along a length thereof.

43. The system of claim 42 wherein the lumen has a distal end disposed near the distal end of the tissue cutting element.

44. The system of claim 28 wherein the locator element deployment tube comprises a distal end having a locator element cold forming die.

45. The system of claim 44 wherein the die is adapted to plastically deform the distal portion of the locator element into an arcuate shape.

46. The system of claim 44 wherein the die defines a die cavity having a reverse curve and a positive curve for plastically deforming the distal portion of the locator element into an arcuate shape.

47. The system of claim 44 wherein the die comprises a lower portion and an upper portion that is axially adjustable with respect to the lower portion.

48. The system of claim 47 wherein the die forms the distal portion of the locator element into a plurality of arcuate shapes.

49. A method for fixedly placing a removable locator element in tissue,
comprising the steps of:
penetrating through tissue at a first site with a deployment tube containing a locator element slideably contained within a lumen of the deployment tube, said locator element having proximal and distal portions, to a position adjacent a targeted tissue volume;. and
advancing the locator element through a distal end of the deployment tube and penetrating tissue so that the distal portion of the locator element defines a tissue border along a first path, the tissue border defining a volume of tissue containing a target region that is substantially bounded but not penetrated by the locator element, and the proximal portion of the locator element extends away from the bound tissue volume.

50. The method of claim 49 additionally comprising the step of proximally withdrawing the locator element from the tissue after the locator element is advanced to define the tissue border.

51. The method of claim 50 additionally comprising the step of re-advancing the locator element through a distal end of the tube and penetrating the tissue.

52. The method of claim 49 wherein the distal portion of the locator element is placed in the tissue border under x-ray guidance.

53. The method of claim 49 wherein the distal portion of the locator element is placed in the tissue border under stereotactic x-ray guidance.

54. The method of claim 49 wherein the distal portion of the locator element is placed in the tissue border under ultrasonic guidance.

55. The method of claim 49 wherein the distal portion of the locator element is placed in the tissue border under magnetic resonance imaging guidance.

56. The method of claim 49 additionally comprising the step of advancing a second locator element through the distal end of the deployment tube and penetrating tissue so that the distal portion of the second locator element further defines the tissue border along a second path,
said second path defining a second plane that is non-parallel to a first plane defined by the first locator element.

57. The method of claim 56 wherein the second plane is angularly displaced approximately ninety degrees with respect to the first plane.

58. The method of claim 56 wherein the second plane is angularly displaced approximately forty-five degrees with respect to the first plane.

59. The method of claim 56 additionally comprising the step of advancing a third locator element through the distal end of the deployment tube and penetrating tissue so that the distal portion of the third locator element further defines the tissue border along a third path,
said third path defining a third plane that is non-parallel to the first plane and the second plane.

60. The method of claim 59 wherein the third plane is angularly displaced approximately forty-five degrees with respect to each of the first and the second planes.

61. The method of claim 49 additionally comprising the step of excising the volume of tissue defined by the tissue locator element.

62. The method of claim 61 wherein the step of excising the volume of tissue is accomplished by surgically accessing the locator element and cutting tissue substantially along a surface of the locator element opposite a surface of the locator element disposed immediately adjacent the tissue volume.

63. The method of claim 62 wherein the step of surgically accessing the locator element is performed by penetrating through the tissue at a second site.

64. The method of claim 62 wherein the step of surgically accessing the locator element is performed circumareolarly in breast tissue.

65. The method of claim 62 wherein the step of surgically accessing the locator element is performed substantially along the locator element deployment tube.

66. The method of claim 62 wherein the step of surgically accessing the locator element is performed substantially along the locator element.

67. The method of claim 61 wherein the step of excising the volume of tissue is accomplished by at least partially energizing the locator element with radio frequency energy and rotating the tissue locator element through an angular displacement.

68. A tissue localizing device comprising:
at least one locator element, said locator element having a non-circular cross-section and being adapted to penetrate tissue so that at least a portion of the locator element defines a tissue border along a first path, the tissue border defining a volume of tissue containing a target region that is substantially bounded by the locator element.

69. The tissue localizing device of claim 68 additionally comprising a second locator element adapted to penetrate tissue so that at least a portion of the second locator element further defines the tissue border along a second path, the target region substantially bounded but not penetrated by the second locator element.

70. The tissue localizing device of claim 68 additionally comprising a deployment tube having a lumen in which the locator element is slideably disposed and a distal end through which the locator element is adapted to exit.

71. The tissue localizing device of claim 70 additionally comprising a second locator element adapted to be slideably disposed in the deployment tube.

72. The tissue localizing device of claim 71 wherein the second locator element is adapted to deploy into the tissue such that the second locator element defines a second plane that is non-parallel to a first plane defined by the first locator element.

73. The tissue localizing device of claim 72 wherein the second plane is angularly displaced approximately ninety degrees with respect to the first plane.

74. The tissue localizing device of claim 72 wherein the second plane is angularly displaced approximately forty-five degrees with respect to the first plane.

75. The tissue localizing device of claim 68 wherein the locator element is at least partially radiopaque.

76. The tissue localizing device of claim 68 wherein a longitudinal axis of a proximal portion of the locator element is adapted to be substantially aligned with a radial axis of a loop formed by the locator element when the locator element is deployed in the tissue volume.

77. The tissue localizing device of claim 68 wherein a longitudinal axis of a proximal portion of the locator element is adapted to be substantially aligned with a tangential axis of a loop formed by the locator element when the locator element is deployed in the tissue volume.

78. The tissue localizing device of claim 68 wherein the locator element comprises a ribbon.

79. The tissue localizing device of claim 68 wherein a width of the locator element is larger than a thickness of the locator element.

80. The tissue localizing device of claim 68 wherein the locator element comprises a wire.

81. The tissue localizing device of claim 80 wherein the wire has a non-circular cross section.

82. The tissue localizing device of claim 68 additionally comprising a suture attached to a proximal end of the locator element.

83. The tissue localizing device of claim 68 wherein the locator element comprises a material selected from the group of stainless steel, spring steel, nickel-titanium, or biocompatible polymer.

84. The tissue localizing device of claim 68 wherein the locator element at least partially comprises a shape memory material.

85. The tissue localizing device of claim 68 wherein the locator element is plastically deformed while defining the tissue border.

86. The tissue localizing device of claim 68 wherein the locator element additionally comprises a distal portion and a shoulder portion disposed proximally of the distal portion.

87. The tissue localizing device of claim 86 wherein the locator element comprises a proximal portion disposed proximally of the shoulder portion, the proximal portion having a smaller cross-sectional area than a cross-sectional area of the distal portion.

88. The tissue localizing device of claim 68 wherein the locator element has a cutting surface.

89. A device for defining the border of a volume of tissue having a proximal portion and a distal portion, the device comprising:
at least one locator element adapted to penetrate tissue proximal to the tissue volume and follow a path to include the distalmost portion of the tissue volume, said locator element having a non-circular cross section.

90. The device of claim 89 wherein the locator element comprises a ribbon.

91. The device of claim 89 wherein a width of the locator element is larger than a thickness of the locator element.

92. The device of claim 89 wherein the locator element is further adapted such that when a proximal portion of the locator element is manipulated, a target region contained within the tissue volume that is substantially bounded by the locator element is correspondingly manipulated.

93. The device of claim 89 wherein the path the locator element is adapted to form a loop when deployed in tissue.

94. A tissue localization system comprising:
a locator element deployment tube and
at least one locator element, said locator element having a non-circular cross section and being positionable within and deployable from the locator element deployment tube and, upon deployment, adapted to penetrate tissue so that at least a portion of the locator element defines a tissue border along a first path, the tissue border defining a volume of tissue containing a target region that is substantially bounded by the locator element.

95. The system of claim 94 additionally comprising an orientation element attached to the locator element deployment tube.

96. The system of claim 95 wherein the orientation element is rotatable with respect to a tissue coordinate system.

97. The system of claim 96 wherein the orientation element is rotatable in fixed angular increments.

98. The system of claim 94 additionally comprising a source of energy connected to the locator element.

99. The system of claim 98 wherein the energy source is electrical.

100. The system of claim 99 wherein the energy is radio frequency energy.

101. The system of claim 98 wherein the source of energy is thermal.

102. The system of claim 98 wherein the source of energy is acoustic.

103. The system of claim 98 wherein the source of energy is mechanical.

104. The system of claim 98 wherein the locator element is partially electrically insulated.

105. The system of claim 104 wherein the locator element has a rectangular cross section having four sides and wherein at least two of the four sides are electrically insulated.

106. The system of claim 104 wherein an electrically insulative material is disposed on at least a portion of a surface of the locator element.

107. The system of claim 104 wherein the electrically insulative material has a low coefficient of friction.

108. The system of claim 94 wherein the cutting element additionally comprises at least one lumen disposed along a length thereof.

109. The system of claim 108 wherein the lumen has a distal end disposed near a distal end of the tissue cutting element.

110. The system of claim 94 wherein the locator element deployment tube comprises a distal end having a locator element cold forming die.

111. The system of claim 110 wherein the die is adapted to plastically deform the locator element into an arcuate shape.

112. The system of claim 110 wherein the die defines a die cavity having a reverse curve and a positive curve for plastically deforming the locator element into an arcuate shape.

113. The system of claim 110 wherein the die comprises a lower portion and an upper portion that is axially adjustable with respect to the lower portion.

114. The system of claim 113 wherein the die forms the locator element into a plurality of arcuate shapes.

115. A method for fixedly placing a removable locator element in tissue, comprising the steps of:

penetrating through tissue at a first site with a deployment tube containing a locator element slideably contained within a lumen of the deployment tube, said locator element having a non-circular cross section, to a position adjacent a targeted tissue volume; and advancing the locator element through a distal end of the deployment tube and penetrating tissue so that at least a portion of the locator element defines a tissue border along a first path, the tissue border defining a volume of tissue containing a target region that is substantially bounded but not penetrated by the locator element.

116. The method of claim 115 additionally comprising the step of proximally withdrawing the locator element from the tissue after the locator element is advanced to define the tissue border.

117. The method of claim 116 additionally comprising the step of re-advancing the locator element through a distal end of the tube and penetrating the tissue.

118. The method of claim 115 wherein the locator element is placed in the tissue border under x-ray guidance.

119. The method of claim 115 wherein the locator element is placed in the tissue border under stereotactic x-ray guidance.

120. The method of claim 115 wherein the locator element is placed in the tissue border under ultrasonic guidance.

121. The method of claim 115 wherein the locator element is placed in the tissue border under magnetic resonance imaging guidance.

122. The method of claim 115 additionally comprising the step of advancing a second locator element through the distal end of the deployment tube and penetrating tissue so that at least a portion of the second locator element further defines the tissue border along a second path, said second path defining a second plane that is non-parallel to a first plane defined by the first locator element.

123. The method of claim 122 wherein the second plane is angularly displaced approximately ninety degrees with respect to the first plane.

124. The method of claim 122 wherein the second plane is angularly displaced approximately forty-five degrees with respect to the first plane.

125. The method of claim 122 additionally comprising the step of advancing a third locator element through the distal end of the deployment tube and penetrating tissue so that at least a portion of the third locator element further defines the tissue border along a third path, said third path defining a third plane that is non-parallel to the first plane and the second plane.

126. The method of claim 125 wherein the third plane is angularly displaced approximately forty-five degrees with respect to each of the first and the second planes.

127. The method of claim 115 additionally comprising the step of excising the volume of tissue defined by the tissue locator element.

128. The method of claim 127 wherein the step of excising the volume of tissue is accomplished by surgically accessing the locator element and cutting tissue substantially along a surface of the locator element opposite a surface of the locator element disposed immediately adjacent the tissue volume.

129. The method of claim 128 wherein the step of surgically accessing the locator element is performed by penetrating through the tissue at a second site.

130. The method of claim 128 wherein the step of surgically accessing the locator element is performed circumareolarly in breast tissue.

131. The method of claim 128 wherein the step of surgically accessing the locator element is performed substantially along the locator element deployment tube.

132. The method of claim 128 wherein the step of surgically accessing the locator element is performed substantially along the locator element.

133. The method of claim 127 wherein the step of excising the volume of tissue is accomplished by at least partially energizing the locator element with radio frequency energy and rotating the tissue locator element through an angular displacement.

134. The tissue localizing device of claim 68 wherein the locator element is adapted to form a loop in the tissue.

\* \* \* \* \*